(12) United States Patent
Kim et al.

(10) Patent No.: US 11,958,885 B2
(45) Date of Patent: Apr. 16, 2024

(54) METHODS FOR DETERMINING A RAPID PROGRESSION RATE OF AMYOTROPHIC LATERAL SCLEROSIS (ALS) AND RESTORING PHAGOCYTIC FUNCTION OF MICROGLIA THEREOF USING A NCK-ASSOCIATED PROTEIN 1 (NCKAP1) PROTEIN OR AN MRNA THEREOF

(71) Applicants: Industry-University Cooperation Foundation Hanyang University, Seoul (KR); CHA UNIVERSITY INDUSTRY-ACADEMIC COOPERATION FOUNDATION, Pocheon-si (KR)

(72) Inventors: Seung Hyun Kim, Seoul (KR); Min Young Noh, Seoul (KR); Min Soo Kwon, Seoul (KR); Ki Wook Oh, Seoul (KR); Min Yeop Nahm, Seoul (KR); Soo Jung Lee, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 154 days.

(21) Appl. No.: 16/651,783

(22) PCT Filed: Aug. 23, 2018

(86) PCT No.: PCT/KR2018/009725
§ 371 (c)(1),
(2) Date: Mar. 27, 2020

(87) PCT Pub. No.: WO2019/066263
PCT Pub. Date: Apr. 4, 2019

(65) Prior Publication Data
US 2020/0247854 A1  Aug. 6, 2020

(30) Foreign Application Priority Data

Sep. 27, 2017 (KR) .......................... 10-2017-0125341

(51) Int. Cl.
*A61K 38/00* (2006.01)
*A61K 38/16* (2006.01)
*A61K 49/00* (2006.01)
*C07K 14/00* (2006.01)
*C07K 14/435* (2006.01)
*C07K 14/46* (2006.01)
*C07K 14/47* (2006.01)
*C12N 15/00* (2006.01)
*C12N 15/62* (2006.01)
*C12N 15/63* (2006.01)
(Continued)

(52) U.S. Cl.
CPC .......... *C07K 14/435* (2013.01); *C12Q 1/6883* (2013.01); *A61K 38/00* (2013.01)

(58) Field of Classification Search
CPC ........... G01N 33/5023; G01N 2510/00; G01N 2500/10; G01N 2800/50; G01N 33/68; G01N 2800/28; G01N 2800/2821; G01N 33/5058; G01N 33/5088; G01N 33/6872; G01N 2800/56; C07K 14/47; C12Q 2600/118; C12Q 2600/158; C12Q 2600/112; C12Q 1/6883; C12Q 1/6851; C12Q 1/6809; C12Q 1/6876; A61P 25/28
See application file for complete search history.

(56) References Cited

U.S. PATENT DOCUMENTS 8,586,006 B2 * 11/2013 Hood ..................... G01N 33/68
424/9.2
10,718,785 B2 * 7/2020 Pike ......................... C12N 9/90
(Continued)

FOREIGN PATENT DOCUMENTS

| CA | 2314909 | * 12/1998 |
| EP | 1 038 958 A1 | 9/2000 |
| WO | WO2007/106507 | * 9/2007 |

OTHER PUBLICATIONS

Hondius et al., Alzheimer's & Dementia, 2016; 12:654-668.*
(Continued)

*Primary Examiner* — Chang-Yu Wang
(74) *Attorney, Agent, or Firm* — Sughrue Mion, PLLC

(57) ABSTRACT

The present invention relates to a novel use of NCKAP1 gene in neurodegenerative diseases. More specifically, the present invention relates to a marker composition for predicting the prognosis of a neurodegenerative disease, comprising a NCKAP1 protein or a gene encoding same, a composition and a kit for predicting the prognosis of a neurodegenerative disease, which comprises a formulation for measuring the level of the protein or an mRNA of the gene encoding same, and a pharmaceutical composition for preventing or treating neurodegenerative disease, comprising the protein or the gene encoding same as an active ingredient. The pharmaceutical composition comprising the NCKAP1 protein or the gene encoding the same, according to the present invention, can selectively control only specific signal transduction related to the phagocytosis of microglial cells unlike conventional therapeutic agents that induce immunosuppression, and thus can be usefully used for the development of therapeutic agents with high safety and efficiency, and the NCKAP1 protein or the gene encoding the same may be usefully utilized, as a marker for predicting the prognosis of a neurodegenerative disease, for predicting a disease progression rate and treatment outcome.

3 Claims, 13 Drawing Sheets

Specification includes a Sequence Listing.

(51) Int. Cl.
*C12Q 1/68* (2018.01)
*C12Q 1/6883* (2018.01)

(56) References Cited

U.S. PATENT DOCUMENTS

| | | | | |
|---|---|---|---|---|
| 10,772,928 | B2* | 9/2020 | Blencowe | A61P 25/18 |
| 2002/0098511 | A1* | 7/2002 | Heichman | C12N 9/1205 435/7.1 |
| 2014/0304845 | A1* | 10/2014 | Loboda | C12Q 1/6883 800/12 |
| 2016/0265057 | A1* | 9/2016 | Smith | G01N 33/6896 |
| 2016/0281085 | A1 | 9/2016 | Chernova | |
| 2017/0360873 | A1* | 12/2017 | Blencowe | A61K 31/713 |
| 2018/0067133 | A1* | 3/2018 | Pike | A61K 31/13 |

OTHER PUBLICATIONS

NCKAP1-MeSH from NCBI website: www.ncbi.nlm.nih.gov/mesh/67098500 retrieved on Jan. 30, 2021.*
Yamanoto et al. Neurosc. Lett. 2001; 316:50-54.*
Zhai et al. FEBS J. 2009; 276:3308-3323.*
Mattson, Nat. Rev. Mol. Cell Biol. 2000; 1:120-129.*
Chen et al. Brain Res. 2010; 1340:52-69.*
The factsheet of NCKAP1 from Uniprot website: www.uniprot.org/uniprot/Q9Y2A7 retrieved on Apr. 10, 2021.*
Hondius Alzheimer & Dementia, 2016; 12:654-662.*
Saris et al. Amy. Troph. Scler. Front. Degen. 2013; 14:190-198.*
Lederer et aal. BMC Genomics, 2007; 8:26. doi:10.1186/1471-2164-8-26.*
Suzuki et al. Genomics, 2000; 63:246-254.*
Noh et al. defective phagocytic function of induced microglia-like cells is correlated with rapid progression of sporadic ALS. published May 23, 2020. doi.org/10.21203/rs.3.rs-29976/v1.*
Konig et al. Cell 2008; 135:49-60. doi:10.1016/j.cell.2008.07.032.*
Royer et al. IAI, 2013; 81:4299-4310.*
Zhuang, Master Thesis, Apr. 2017. Bioinformatics, Univeristy of British Columbia2009.*
Morello et al. Mediators in Inlammation, 2017 article ID 7070469. doi.org/10.1155/2017/7070469.*
Alonso-Gonzalez et al. Front. Genetics. published Sep. 21, 2018; doi: 10.3389/fgene.2018.00406.*
Williams et al.,Nat. Commun. 2016;7:11253. DOI:10.1038/ncomms11253.*
Ranganathan et al.,Front. in Neurosci. 2020; doi:10.3389/fnins.2020.00684.*
Ju et al., PLoS Biology 2011; 9: 1-17; e1001052.*
Lagier-Tourenne et al., Human Mol. Genet. 2010; 19: R46-R64 published online Apr. 15, 2010; doi: 10.1093/hmg/ddq137.*
Bruijn et al., Annu. Rev. Neurosci. 2004, 27: 723-49.*
NCBI GenBank Accession No. NM_013436.4, "*Homo sapiens* NCK Associated Protein 1 (NCKAP1), Transcript Variant 1, mRNA", 28 Aug. 28, 2016, 8 pages.
NCBI, GenBank Accession No. NP_38464.1, "Nck-associated protein 1 isoform 1 [*Homo sapiens*]", Jan. 17, 2016, 4 pages.
Li Du, et al., "Role of Microglia in Neurological Disorders and Their Potentials as a Therapeutic Target", Mol Neurobiol, Nov. 9, 2016, 18 pages.
International Search Report for PCT/KR2018/009725 dated Nov. 30, 2018 [PCT/ISA/210].
Myung S. Yoo et al., "Oxidative stress regulated genes in nigral dopaminergic neuronal cells: correlation with the known pathology in Parkinson's disease", Molecular Brain Research, 2003, vol. 110, pp. 76-84 (9 pages) XP 55589585A.
Ayako Yamamoto et al., "Isolation of hNap1BP which interacts with human Nap1 (NCKAP1) whose expression is down-regulated in Alzheimer's disease", Gene, 2001, vol. 271, pp. 159-169 (11 pages) XP 4246887A.
Extended European Search Report dated May 20, 2021, issued by the European Patent Office in application No. 18862617.0.
NCBI GenBank Accession No. NM_013436.5, "*Homo sapiens* NCK Associated Protein 1 (NCKAP1), Transcript Variant 1, mRNA", May 2, 2019, 8 pages.

* cited by examiner

[Fig. 1]
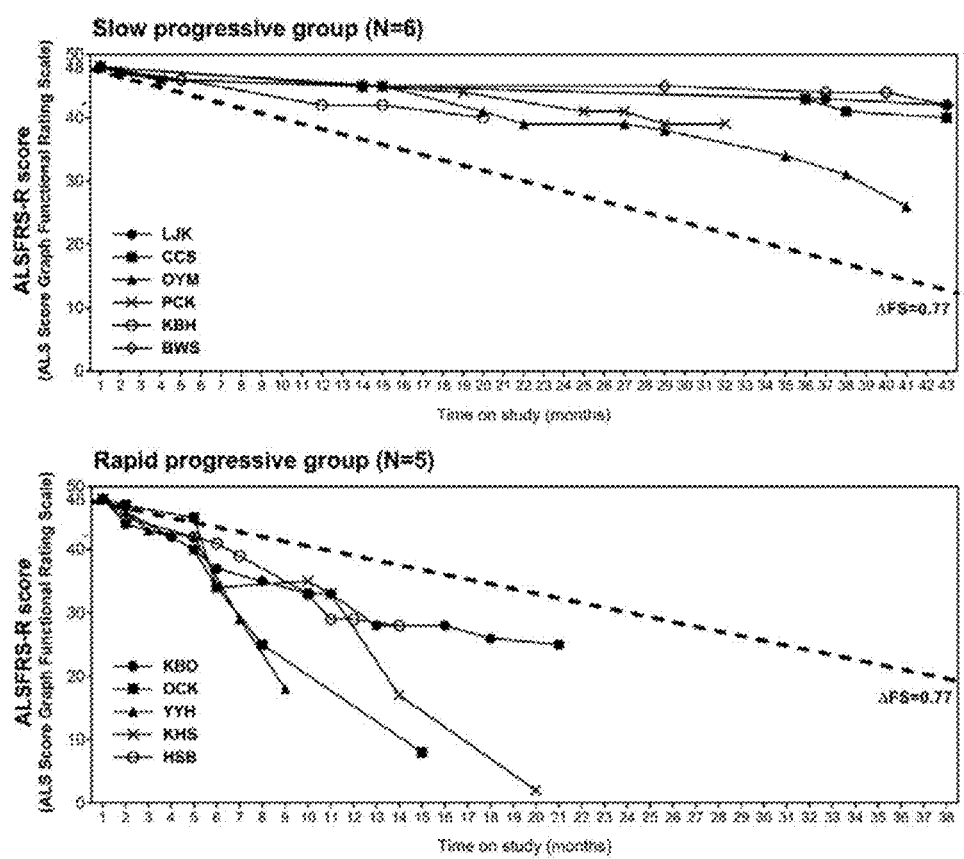

[Fig. 2A]
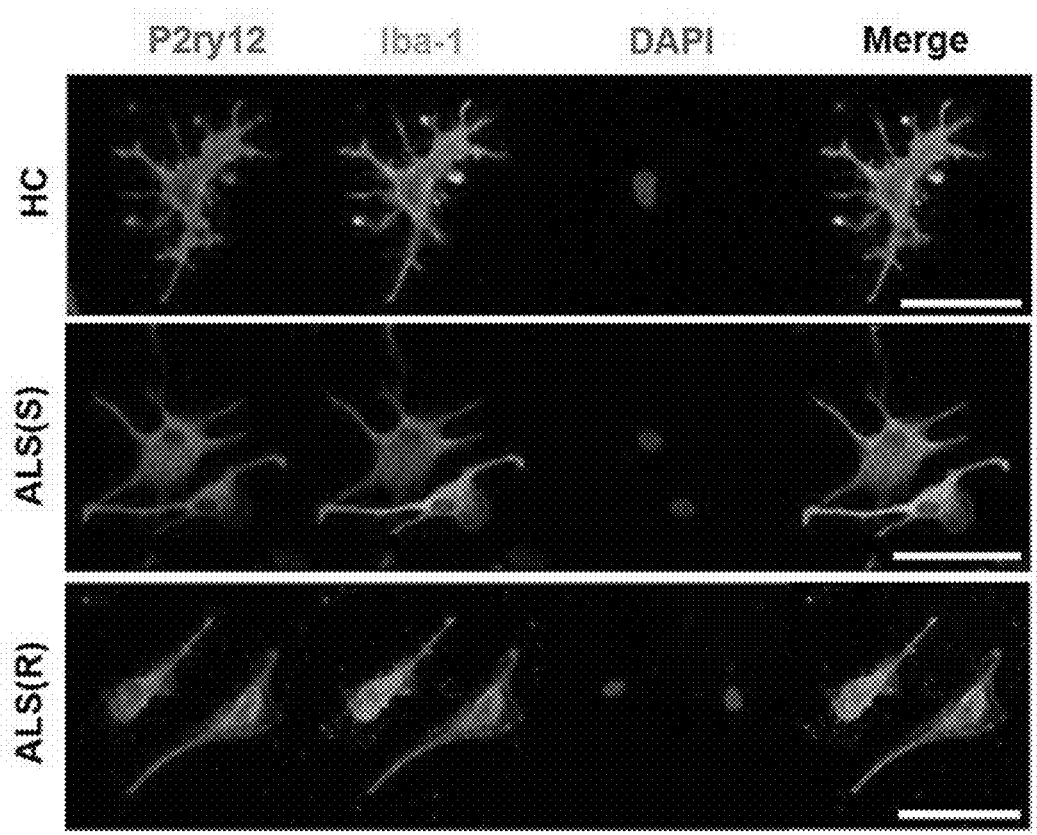

[Fig. 2B]
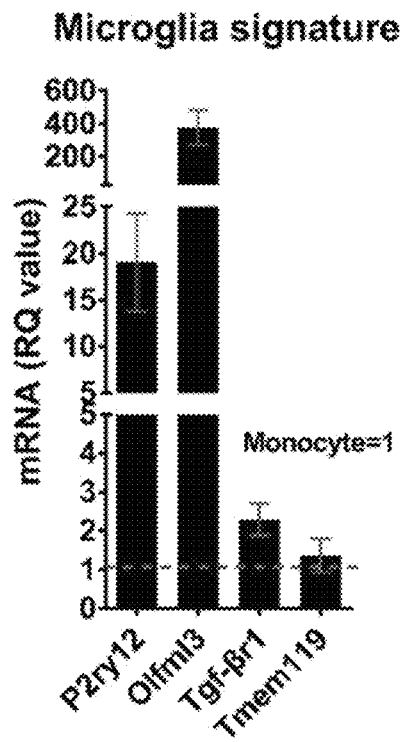
[Fig. 2C]
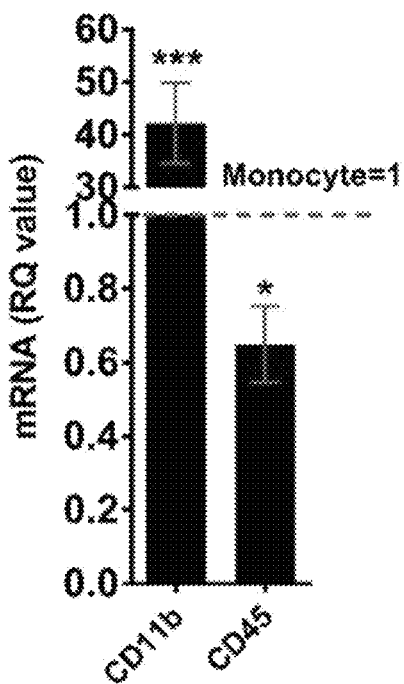

[Fig. 3A]
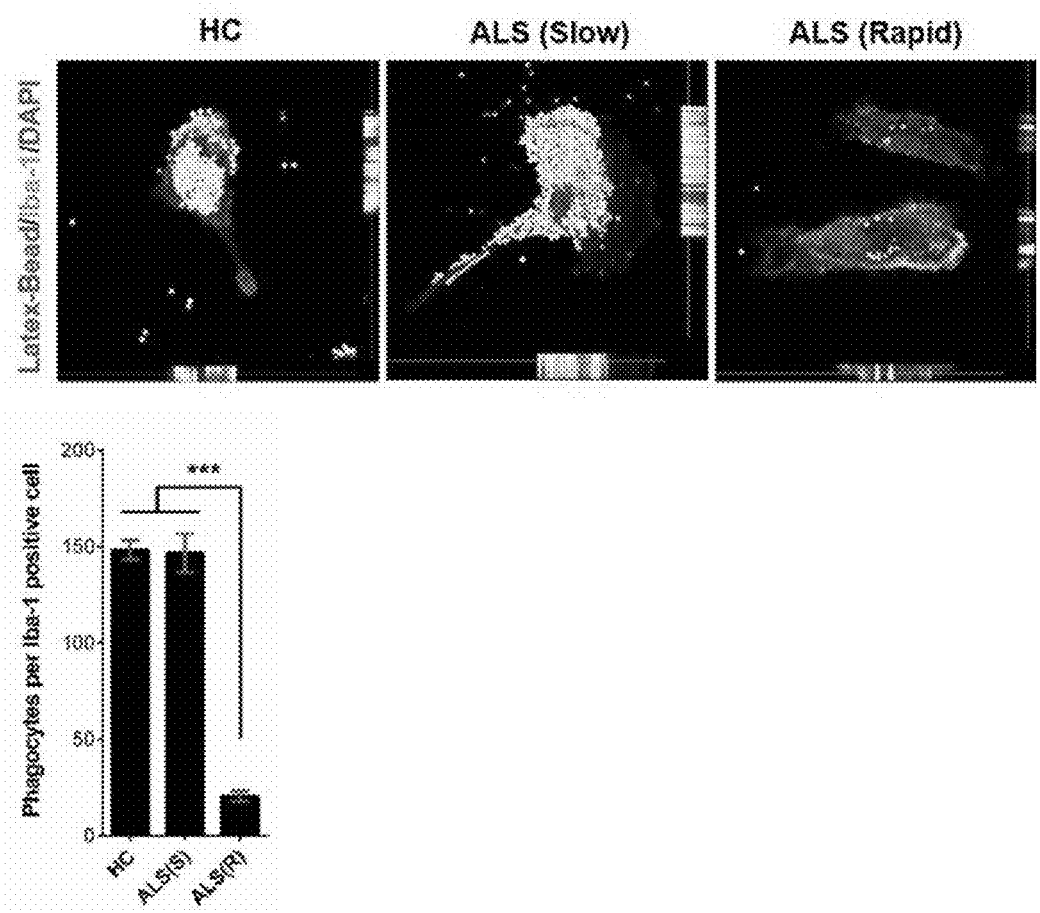

[Fig. 3B]
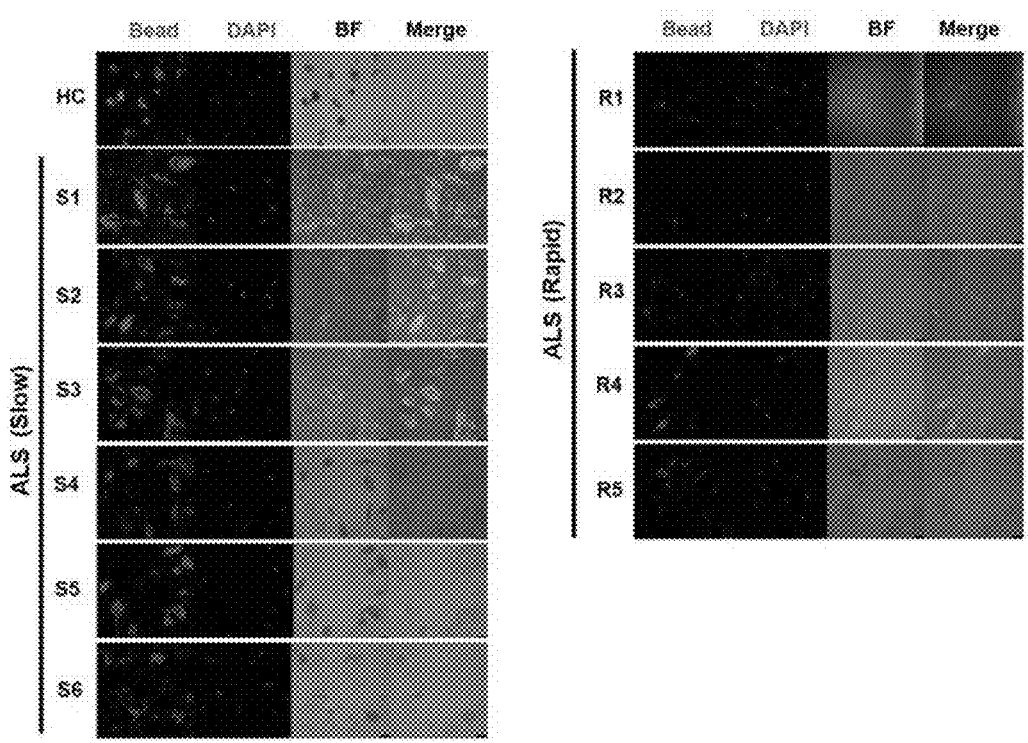

[Fig. 4A]
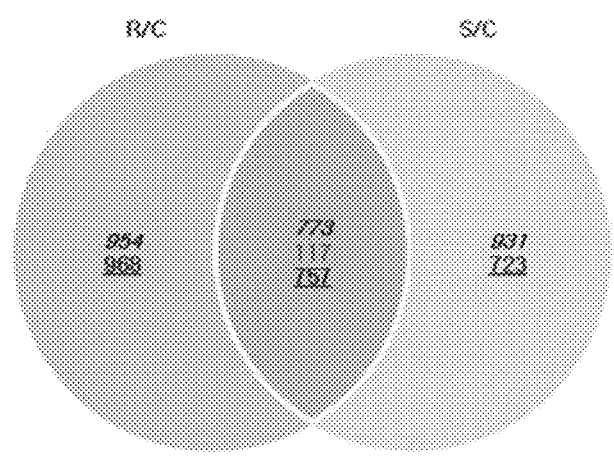

[Fig. 4B]
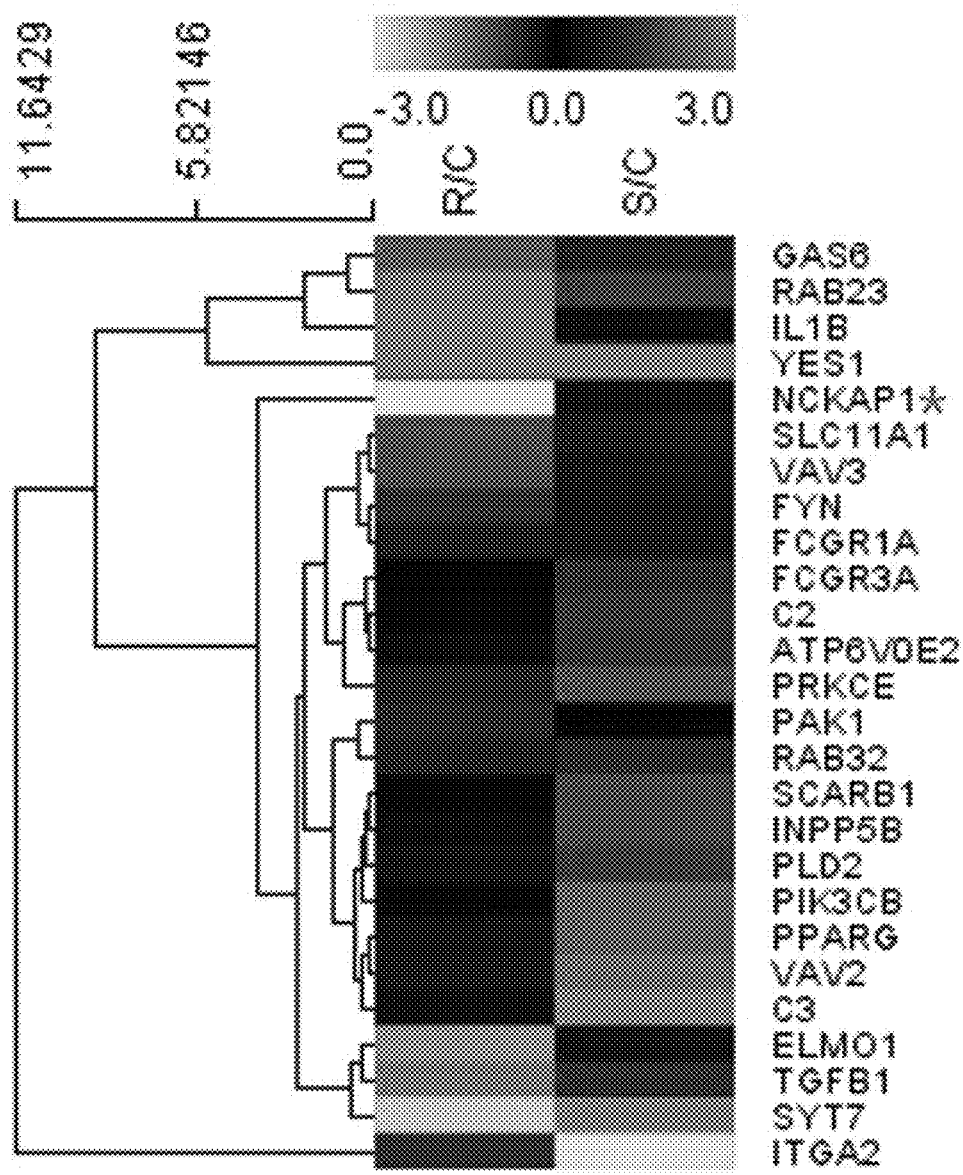

【Fig. 5A】
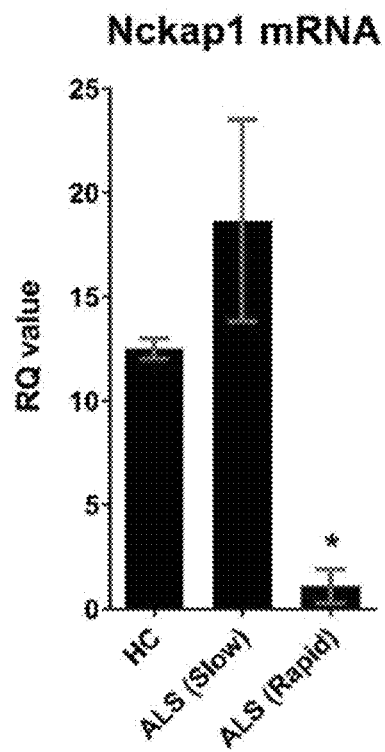
【Fig. 5B】
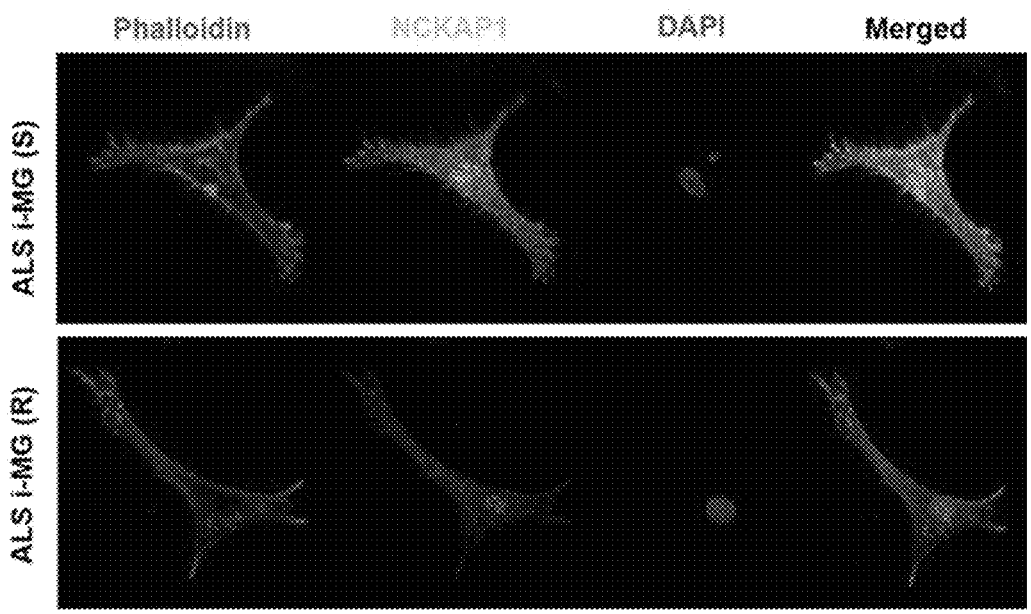

[Fig. 6]
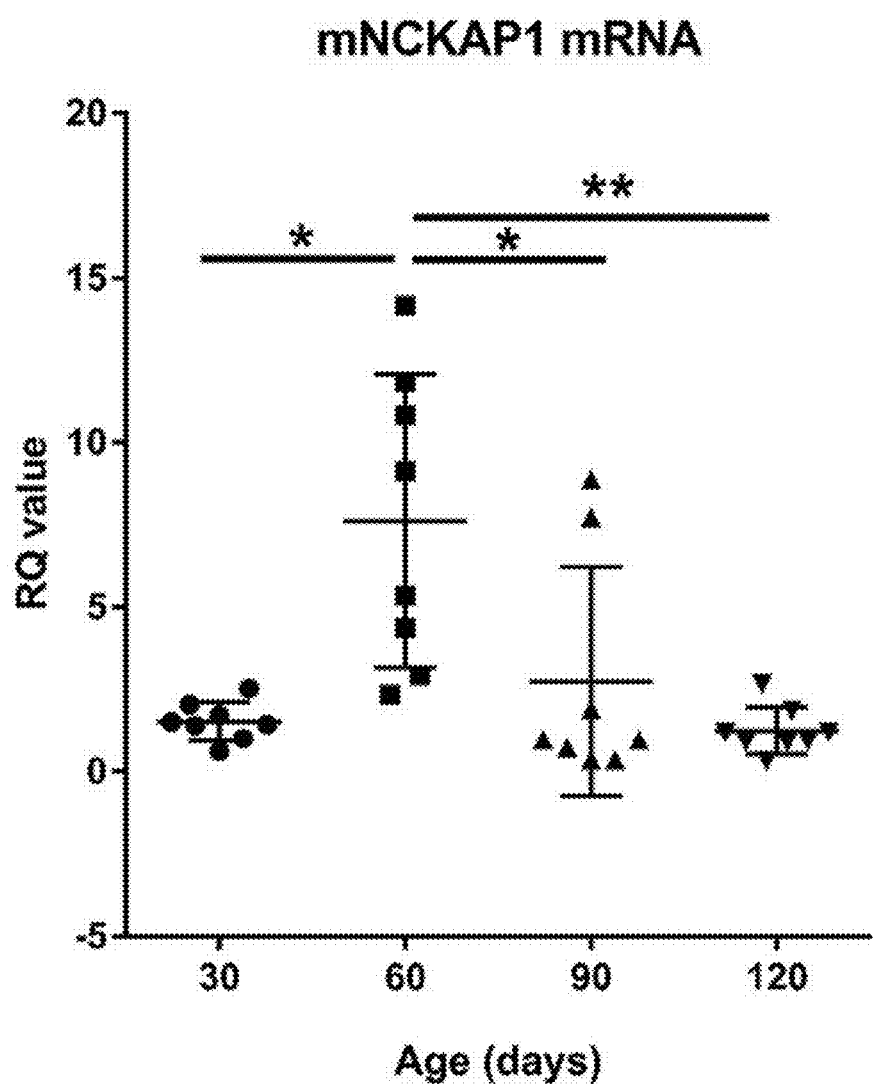

【Fig. 7】
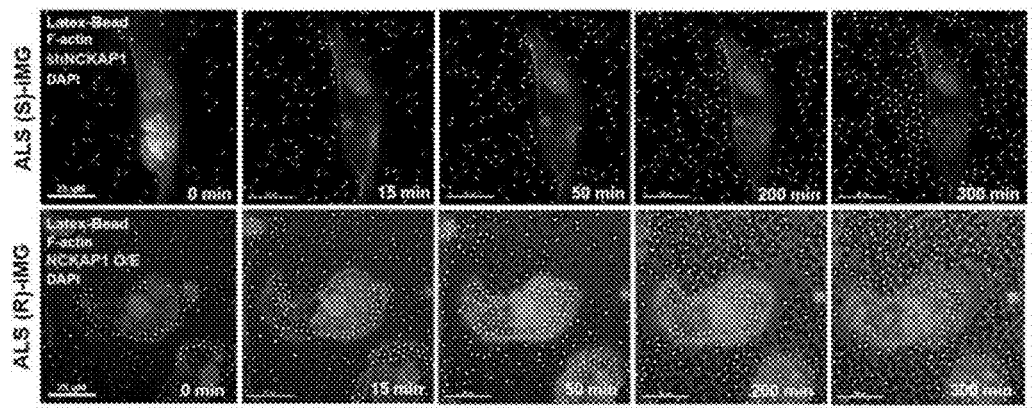
【Fig. 8】
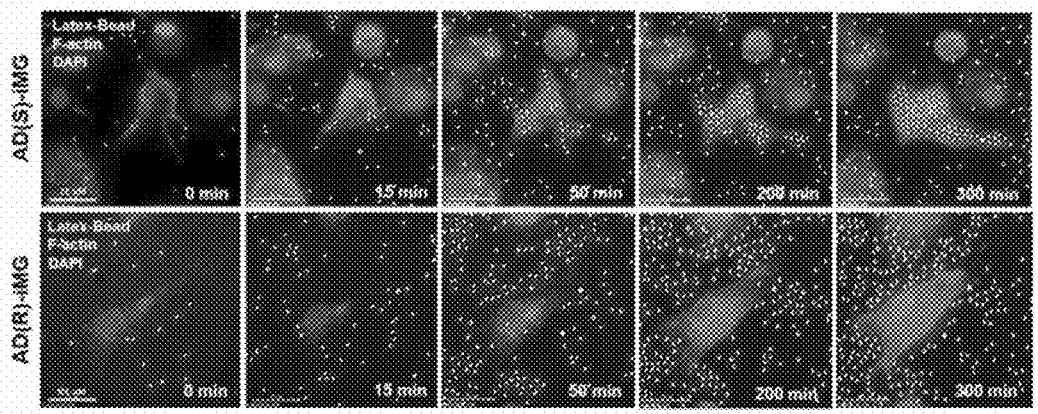

[Fig. 9]
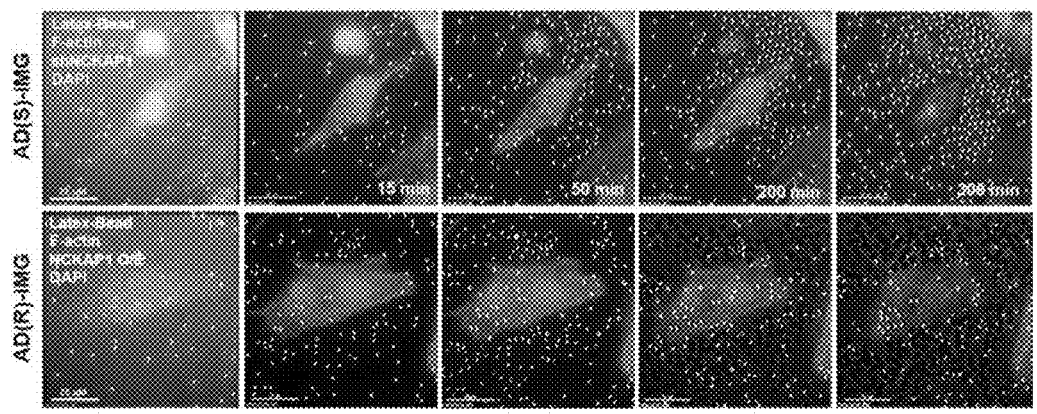

[Fig. 10A]
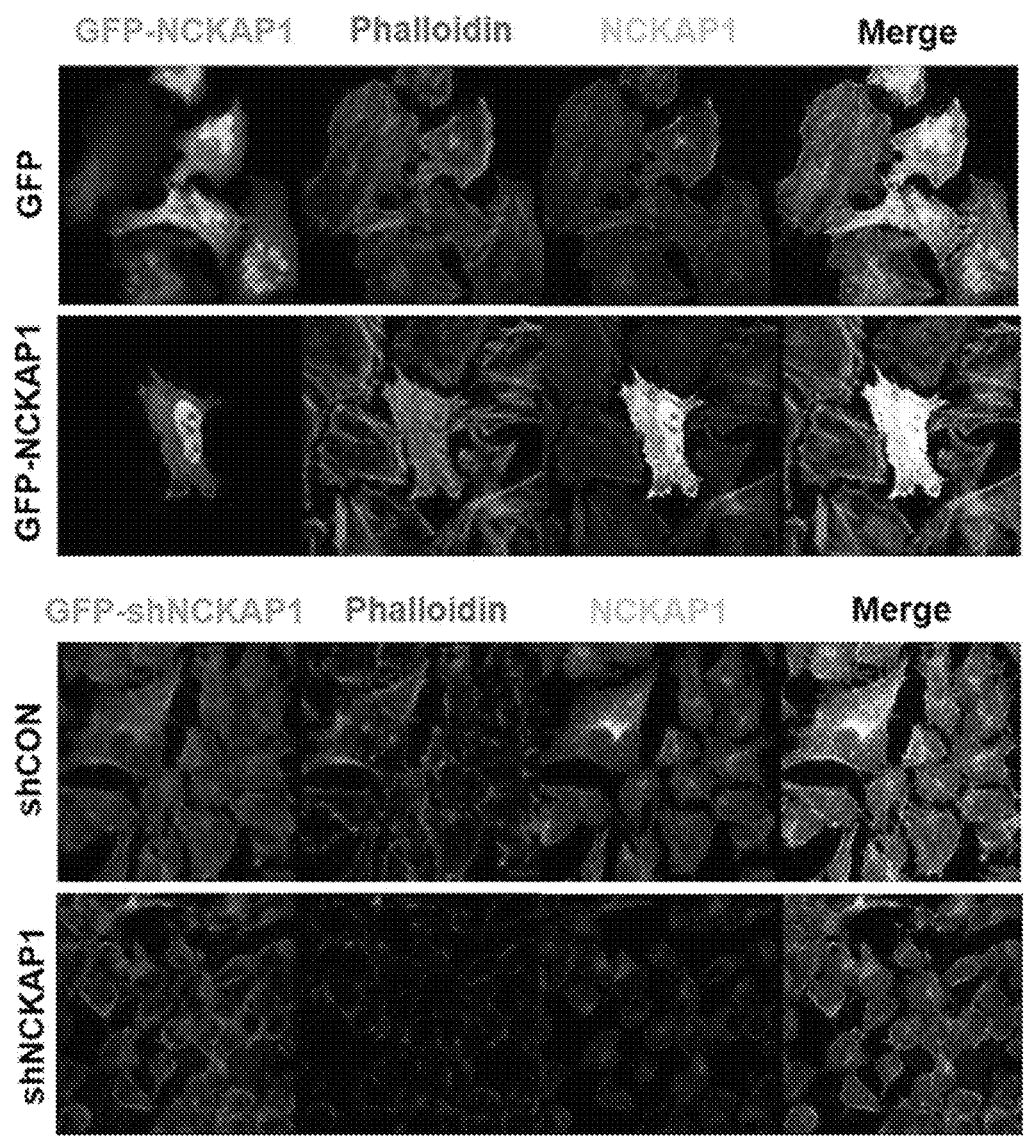

[Fig. 10B]
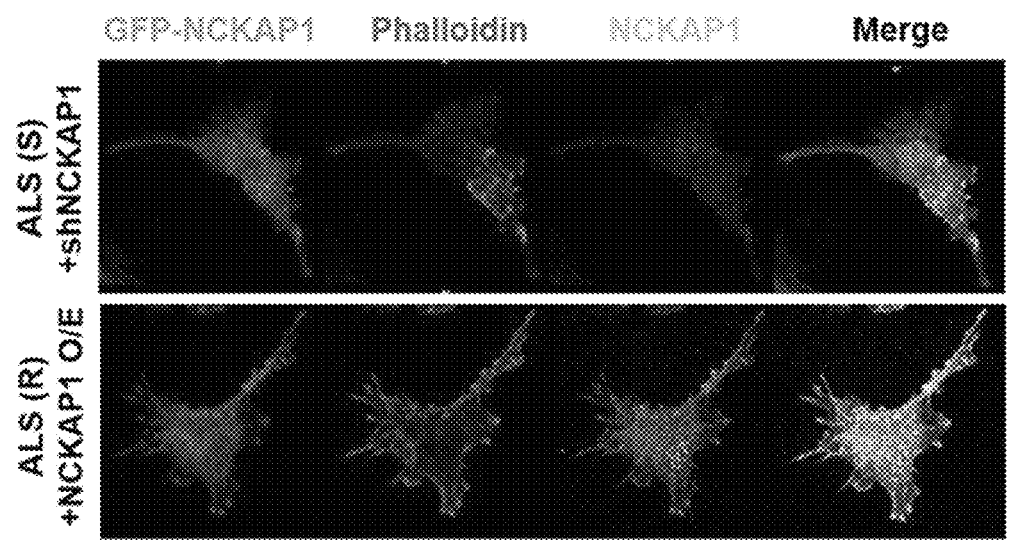
[Fig. 11]
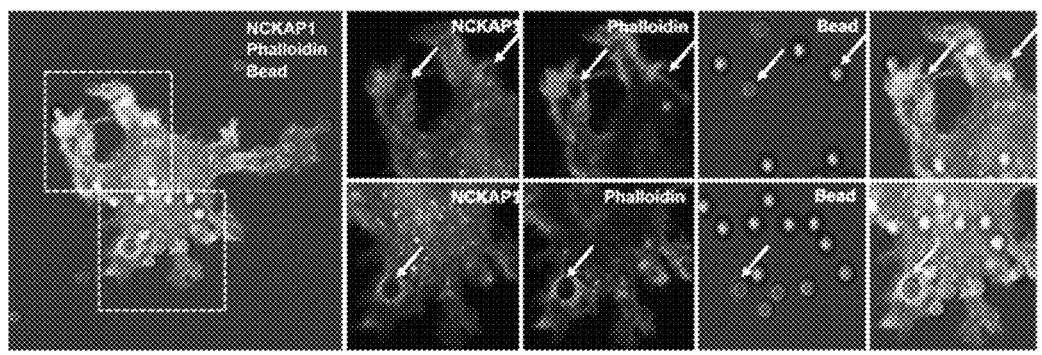

METHODS FOR DETERMINING A RAPID PROGRESSION RATE OF AMYOTROPHIC LATERAL SCLEROSIS (ALS) AND RESTORING PHAGOCYTIC FUNCTION OF MICROGLIA THEREOF USING A NCK-ASSOCIATED PROTEIN 1 (NCKAP1) PROTEIN OR AN MRNA THEREOF

CROSS REFERENCE TO RELATED APPLICATIONS

This application is a National Stage of International Application No. PCT/KR2018/009725, filed on Aug. 23, 2018, which claims priority from Korean Patent Application No. 10-2017-0125341, filed on Sep. 27, 2017.

TECHNICAL FIELD

The present invention relates to a novel use of the NCKAP1 gene in neurodegenerative diseases, and more particularly to a marker composition for predicting the prognosis of a neurodegenerative disease which includes the NCKAP1 protein or a gene encoding the protein, a composition and kit for predicting the prognosis of a neurodegenerative disease which include a formulation for measuring the level of the protein or an mRNA of a gene encoding the same, and a pharmaceutical composition for the prevention or treatment of a neurodegenerative disease which includes the protein or a gene encoding the same as an active ingredient.

BACKGROUND ART

A neurodegenerative disease is a disease that causes motor control dysfunction, cognitive dysfunction, perceptual dysfunction, sensory dysfunction, and autonomic dysfunction due to the structural and functional loss of neurons, and in line with the rapid progress in population aging worldwide, the number of patients with neurodegenerative diseases such as amyotrophic lateral sclerosis (ALS), Alzheimer's disease (AD), and Parkinson's disease (PD) is rapidly increasing. In these neurodegenerative diseases, neurons once damaged or killed, often fail to return to their normal state leading to severe aftereffects and continue to worsen due to the nature of neurons being difficult to repair and regenerate. Therefore, to address this, domestic and foreign research has been actively conducted for more than a few decades, but the development of therapeutic agents is still very difficult, and even the exact cause is not adequately identified. Due to these characteristics, most neurodegenerative diseases cannot be cured by current treatment techniques, and the focus is mainly on targeting the neurotransmission process to alleviate symptoms by controlling the progression rate. Therefore, there is an urgent need to develop new therapeutic targets and therapeutic agents for neurodegenerative diseases, and the development of markers capable of diagnosing the disease earlier and predicting the prognosis thereof is also an important task.

In the past, the proliferation of neuroglial cells, the infiltration of inflammation-related immune cells and immune mediators, and the like, which are observed in the pathological findings of neurodegenerative diseases, have been accepted only as nonspecific secondary phenomena resulting from the destruction of neurons. However, advances in molecular biology have made it possible to identify surface markers of cells that play an important role in the immune-inflammatory mechanism, and as the identity and functions of immune-inflammatory mediators have been identified, evidence has shown that the immune-inflammatory mechanism may be involved not only in non-specific secondary responses to neurological damage, but also in the early stage during the progression of neurodegenerative diseases, and will control the degree of pathological phenomena and be actively involved in the survival and death of nerve cells. Thus, these findings provide a basis for the treatment of modulating and inhibiting the immune-inflammatory response as a new therapeutic strategy for degenerative diseases.

Meanwhile, microglia are major cells that affect the neuroinflammation of neurodegenerative diseases, and are involved in brain neuronal integrity and death by synaptic remodeling, the secretion of various nerve growth factors, and the removal of various debris accumulated in the brain, thereby playing an important role in maintaining homeostasis. According to a recent paper, microglia function well under normal conditions, but in neurodegenerative diseases, microglia are activated by various unfolded or aggregated proteins (e.g., amyloid-β and α-synuclein which cause Alzheimer's disease, SOD1 which causes amyotrophic lateral sclerosis, and TDP-43 which induces temporal lobe dementia). In addition, as it has been found that numerical changes and dysfunction act as stimulants of inflammatory responses, which induce neuritis, affecting the onset of and the degree of progression of neurodegenerative diseases, microglial loss or dysfunction is emphasized in neurodegenerative diseases (Mol Neurobiol. 2016 Nov. 9. [Epub ahead of print]). Therefore, attention has been focused on the treatment of neurodegenerative diseases by controlling the function of microglia in addition to existing treatment methods.

DISCLOSURE

Technical Problem

Therefore, as a result of analyzing the function of microglia derived from patients with different degrees of disease progression in patients with amyotrophic lateral sclerosis and Alzheimer's disease, which are typical neurodegenerative diseases, the inventors of the present invention found a reduction in NCKAP1 expression and dysfunction in microglia derived from patients exhibiting a rapid progression rate, and confirmed that the function of microglia was restored by the regulation of NCKAP1 expression, and thus completed the present invention.

Therefore, an object of the present invention is to provide a marker composition for predicting the prognosis of a neurodegenerative disease, which includes the NCK-associated protein 1 (NCKAP1) protein or a gene encoding the protein.

Another object of the present invention is to provide a composition for predicting the prognosis of a neurodegenerative disease, which includes a formulation for measuring a level of the NCK-associated protein 1 (NCKAP1) protein or an mRNA of a gene encoding the protein, and a kit for predicting a prognosis which includes the composition.

Still another object of the present invention is to provide a pharmaceutical composition for preventing or treating a neurodegenerative disease, which includes the NCK-associated protein 1 (NCKAP1) protein or a gene encoding the protein as an active ingredient.

However, technical problems to be solved by the present invention are not limited to the above-described technical problems, and other unmentioned technical problems will become apparent from the following description to those of ordinary skill in the art.

Technical Solution

According to an aspect of the present invention, there is provided a marker composition for predicting the prognosis of a neurodegenerative disease, which includes the NCK-associated protein 1 (NCKAP1) protein or a gene encoding the protein.

The present invention also provides a composition for predicting the prognosis of a neurodegenerative disease, which includes a formulation for measuring a level of the NCK-associated protein 1 (NCKAP1) protein or an mRNA of a gene encoding the protein, and a kit for predicting a prognosis which includes the composition.

In one embodiment of the present invention, the NCKAP1 protein may consist of an amino acid sequence of SEQ ID NO: 1.

In another embodiment of the present invention, the gene encoding the NCKAP1 protein may consist of a nucleotide sequence of SEQ ID NO: 2.

In another embodiment of the present invention, the neurodegenerative disease may be amyotrophic lateral sclerosis, Alzheimer's disease, or Parkinson's disease.

In another embodiment of the present invention, the formulation for measuring a level of the protein may be an antibody specifically binding to the protein encoded by a gene.

In another embodiment of the present invention, the formulation for measuring an mRNA level may be sense and antisense primers, or a probe, which complementarily binds to mRNA of the gene.

The present invention also provides a pharmaceutical composition for preventing or treating a neurodegenerative disease, which includes the NCK-associated protein 1 (NCKAP1) protein or a gene encoding the protein as an active ingredient.

In one embodiment of the present invention, the composition may activate the phagocytic function of microglia through actin polymerization in the cells.

The present invention also provides a method of preventing or treating a neurodegenerative disease, which includes administering the pharmaceutical composition to a subject.

The present invention also provides a use of the pharmaceutical composition for preventing or treating a neurodegenerative disease.

Advantageous Effects

The inventors of the present invention observed that the expression of the NCKAP1 gene was reduced in neurodegenerative disease patient-derived microglia exhibiting phagocytic dysfunction, and experimentally confirmed that the gene was involved in the actin polymerization of microglia, thereby regulating the phagocytic function of the cells. Therefore, the pharmaceutical composition including the NCKAP1 protein or a gene encoding the same according to the present invention selectively modulates only specific signaling related to phagocytosis of microglia, unlike existing therapeutic agents that induce immunosuppression, and thus can be usefully applied to the development of a therapeutic agent with high safety and efficiency, and the NCKAP1 protein or a gene encoding the same can be usefully applied as a marker for predicting the prognosis of a neurodegenerative disease to predict the progression rate and treatment results of the disease.

DESCRIPTION OF DRAWINGS

FIG. 1 shows the characteristics of two groups of amyotrophic lateral sclerosis patients with different degrees of disease progression according to an embodiment of the present invention.

FIG. 2A illustrates the results of confirming the expression of the P2ry12 and iba-1 proteins, which are phenotype markers of microglia, by immunocytochemistry in microglia (ALS(S) and ALS(R)) derived from peripheral blood derived from amyotrophic lateral sclerosis patients having slow and rapid progression rates, respectively.

FIG. 2B illustrates the results of measuring the mRNA expression levels of P2ry12, iba-1, Olfml3, Tgf-βr1, and Tmem119, which are phenotype markers of microglia, through qRT-PCR in microglia derived from peripheral blood derived from amyotrophic lateral sclerosis patients.

FIG. 2C illustrates the results of measuring the mRNA expression levels of CD11b and CD45, which are phenotype markers of microglia, using the same method as that used in FIG. 2B.

FIG. 3A illustrates the immunostaining results of analyzing the phagocytic function of microglia (ALS(Slow) and ALS(Rapid)) derived from peripheral blood derived from amyotrophic lateral sclerosis patients having slow and rapid progression rates, respectively.

FIG. 3B illustrates the immunostaining results of analyzing the stepwise phagocytic function of microglia (ALS (Slow) and ALS(Rapid)) derived from peripheral blood derived from amyotrophic lateral sclerosis patients having slow and rapid progression rates, respectively.

FIG. 4A illustrates the results of analyzing the transcripts of microglia (S/C and R/C) derived from peripheral blood derived from amyotrophic lateral sclerosis patients having slow and rapid progression rates, respectively.

FIG. 4B illustrates heat map results showing a comparison between expression levels of transcripts related to phagocytosis in microglia (S/C and R/C) derived from peripheral blood derived from amyotrophic lateral sclerosis patients having slow and rapid progression rates, respectively.

FIG. 5A illustrates the results of measuring the mRNA level of NCKAP1 through qRT-PCR in microglia (ALS (Slow) and ALS(Rapid)) derived from peripheral blood derived from amyotrophic lateral sclerosis patients having slow and rapid progression rates, respectively.

FIG. 5B illustrates the results of analyzing a level of the NCKAP1 protein through immunostaining in microglia (ALS i-MG(S) and ALS i-MG(R)) derived from peripheral blood derived from amyotrophic lateral sclerosis patients having slow and rapid progression rates, respectively.

FIG. 6 illustrates the results of measuring the expression level of NCKAP1 mRNA according to mouse age, i.e., the progression of amyotrophic lateral sclerosis (30, 60, 90, and 120 (days)) in the spinal cord tissue of an amyotrophic lateral sclerosis-induced mouse model.

FIG. 7 illustrates the results of analyzing changes in phagocytosis of microglia derived from amyotrophic lateral sclerosis patients according to the regulation of NCKAP1 expression, showing, through real-time imaging, changes in phagocytic function after inhibiting (shNCKAP1) and overexpressing (O/E) the expression of NCKAP1 in microglia (ALS (S)-iMG and ALS (R)-iMG) derived from patients having slow and rapid progression rates, respectively.

FIG. 8 illustrates the results showing, through real-time imaging, phagocytosis of microglia (AD (S)-iMG and AD (R)-iMG) derived from peripheral blood derived from Alzheimer's disease patients having slow and rapid progression rates, respectively.

FIG. 9 illustrates the results of analyzing changes in phagocytosis of microglia derived from Alzheimer's disease patients according to the regulation of NCKAP1 expression, showing, through real-time imaging, changes in phagocytic function after inhibiting (shNCKAP1) and overexpressing (O/E) the expression of NCKAP1 in microglia (AD (S)-iMG and AD (R)-iMG) derived from patients having slow and rapid progression rates, respectively.

FIG. 10A illustrates the results showing a change in F-actin protein expression according to the overexpression or expression inhibition of NCKAP1 in Hela cells.

FIG. 10B illustrates the results of analyzing changes in F-actin expression after inhibiting NCKAP1 expression (ALS (S)+shNCKAP1) in microglia derived from patients having a slow progression rate or overexpressing NCKAP1 (ALS (R)+NCKAP1 O/E) in microglia derived from patients having a rapid progression rate.

FIG. 11 illustrates the immunostaining results showing that NCKAP1 was involved in phagocytic cup formation by the actin dynamics in microglia derived from amyotrophic lateral sclerosis patients.

BEST MODE

The inventors of the present invention identified a novel use of NCKAP1 that can be used for predicting the prognosis of and treating neurodegenerative diseases, and thus completed the present invention based on this finding.

Therefore, the present invention provides a marker composition for predicting the prognosis of a neurodegenerative disease, which includes the NCK-associated protein 1 (NCKAP1) protein or a gene encoding the protein.

The present invention also provides a composition for predicting the prognosis of a neurodegenerative disease, which includes a formulation for measuring a level of a NCK-associated protein 1 (NCKAP1) protein or an mRNA of a gene encoding the protein, and a kit for predicting the prognosis of a neurodegenerative disease, which includes the composition.

In the present invention, the NCKAP1 protein may consist of an amino acid sequence of SEQ ID NO: 1, and the gene encoding the protein may consist of a nucleotide sequence of SEQ ID NO: 2.

The "neurodegenerative disease," which is a target disease in the present invention, refers to a disease in which motor control dysfunction, cognitive dysfunction, perceptual dysfunction, sensory dysfunction, and autonomic dysfunction are caused by the structural and functional loss of neurons. When nerve cells are damaged or killed, the cells are difficult to repair and regenerate, which can leave severe aftereffects, and no effective therapeutic agent has been developed to date. Therefore, there is an urgent need to develop a useful marker capable of predicting the progression and treatment outcomes of neurodegenerative diseases and an efficient therapeutic agent having a low risk of side effects. In the present invention, the neurodegenerative disease includes amyotrophic lateral sclerosis, Alzheimer's disease, and Parkinson's disease, but the present invention is not limited thereto.

The term "prognosis" as used herein means the progression of a disease and prediction of recovery therefrom, and refers to an outlook or preliminary evaluation. In the present invention, the prognosis means a prediction about the progression, treatment results, or recovery with respect to neurodegenerative diseases, but the present invention is not limited thereto.

The formulation for measuring a protein level may be an antibody that specifically binds to a protein encoded by a gene, but the present invention is not limited thereto.

The term "antibody" as used herein includes immunoglobulin molecules which are immunologically reactive with a specific antigen, and includes both monoclonal and polyclonal antibodies. In addition, the antibody includes forms produced by genetic engineering, such as chimeric antibodies (e.g., humanized murine antibodies) and heterologous binding antibodies (e.g., bispecific antibodies).

The formulation for measuring an mRNA level may be sense and antisense primers, or probe, which complementarily binds to the mRNA of the gene.

The term "primer" as used herein refers to a short nucleic acid sequence that acts as a point of initiation for DNA synthesis, and means an oligonucleotide synthesized for use in diagnosis, DNA sequencing, and the like. The primers may be generally synthesized to a length of 15 base pairs to 30 base pairs, but may vary according to the purpose of use, and may be modified using a known method, such as methylation, capping, or the like.

The term "probe" as used herein refers to a nucleic acid having a length of several to hundreds of bases and capable of specifically binding to mRNA, wherein the nucleic acid is prepared through enzymatic chemical separation and purification or synthesis. A probe may be labeled with a radioactive isotope, an enzyme, or the like to identify the presence or absence of mRNA, and may be designed and modified using a known method.

The kit for predicting a prognosis according to the present invention consists of one or more types of other components compositions, solutions, or devices suitable for analysis methods.

For example, the kit of the present invention may be a kit including genomic DNA derived from a sample to be analyzed, a primer set specific to a marker gene of the present invention, an appropriate amount of DNA polymerase, a dNTP mixture, a PCR buffer, and water, to perform PCR. The PCR buffer may include KCl, Tris-HCl, and MgCl2. The kit of the present invention may further include, in addition to the above components, components needed for electrophoresis, which may be used to confirm whether a PCR product is amplified.

In addition, the kit of the present invention may be a kit including essential elements needed for performing RT-PCR. An RT-PCR kit may include, in addition to each pair of primers specific to a marker gene, test tubes or other suitable containers, reaction buffers, deoxynucleotides (dNTPs), enzymes such as Taq-polymerases and reverse transcriptases, DNase and RNase inhibitors, DEPC-water, sterile water, and the like. In addition, the RT-PCR kit may include a pair of primers specific to a gene used as a quantitative control.

In addition, the kit of the present invention may be a kit including essential elements needed for performing DNA chip analysis. A DNA chip kit may include a substrate to which cDNA corresponding to a gene or a fragment thereof is attached with a probe, and the substrate may include cDNA corresponding to a quantitative structural gene or a fragment thereof. In addition, the kit of the present invention may be in the form of a microarray having a substrate on which the marker gene of the present invention is immobilized.

In addition, the kit of the present invention may be a kit including essential elements needed for performing ELISA. An ELISA kit includes an antibody specific to a marker protein, and a formulation for measuring a level of the marker protein. The ELISA kit may include a reagent capable of detecting an antibody forming an antigen-antibody complex, for example, a labeled secondary antibody, chromopores, an enzyme, and a substrate of the enzyme. In addition, the ELISA kit may include an antibody specific to a protein as a quantitative control.

The term "antigen-antibody complex" as used herein refers to a combination of a protein encoded by a gene and an antibody specific thereto. The formation amount of the antigen-antibody complex may be quantitatively measured by the intensity of a signal of a detection label. The detection label may be selected from the group consisting of an enzyme, a fluorescent substance, a ligand, a luminescent substance, microparticles, a redox molecule, and a radioactive isotope, but the present invention is not limited thereto.

The present invention also provides a method of providing information for predicting the prognosis of a neurodegenerative disease, including measuring a level of the NCKAP1 protein or an mRNA of a gene encoding the protein in a biological sample derived from a subject.

The biological sample derived from a subject may be, but is not limited to, tissue, cells, whole blood, blood, saliva, sputum, cerebrospinal fluid, and urine, more preferably blood.

The expression level of the protein may be measured using one or more methods selected from western blotting, radioimmunoassay (RIA), radioimmunodiffusion, enzyme linked immunosorbent assay (ELISA), immunoprecipitation, flow cytometry, immunofluorescence, Ouchterlony, complement fixation assay, and protein chips, which are commonly known in the art, but the present invention is not limited thereto.

The mRNA expression level may be measured using one or more methods selected from the group consisting of polymerase chain reaction (PCR), reverse transcription-PCR (RT-PCR), real-time PCR, RNase protection assay (RPA), a microarray, and northern blotting, but the present invention is not limited thereto.

The term "method of providing information for predicting the prognosis of a neurodegenerative disease" is a preliminary process for predicting a prognosis, which provides objective basic information needed for predicting the prognosis of a neurodegenerative disease and excludes clinical determination or findings of a doctor.

The inventors of the present invention confirmed that the expression of NCKAP1 was inhibited in cells showing phagocytic dysfunction in microglia derived from amyotrophic lateral sclerosis patients with different degrees of disease progression, and thus confirmed there was a close correlation between the gene and the dysfunction of patient-derived microglia.

In one embodiment of the present invention, microglia derived from peripheral blood derived from amyotrophic lateral sclerosis patients with different degrees of disease progression were obtained, and as a result of observing the phagocytosis of each case, severe phagocytic dysfunction was observed in microglia derived from patients having a rapid progression rate (see Example 3).

In another embodiment of the present invention, by performing the transcript analysis of microglia derived from amyotrophic lateral sclerosis patients having a slow or rapid progression rate of the disease, it was confirmed that a large number of differentially expressed genes was present, and as a result of comparing expression levels of genes related to phagocytosis of the cells, it was confirmed that the expression of the NCKAP1 gene was significantly reduced in microglia showing phagocytic dysfunction (see Example 4).

In another embodiment of the present invention, as result of measuring the mRNA and protein levels of the gene in microglia derived from amyotrophic lateral sclerosis patients with different levels of disease progression to re-verify the expression level of the NCKAP1 gene, it was confirmed that the expression level was very low in microglia derived from patients showing phagocytic dysfunction and having a rapid progression rate, and that the mRNA level of the gene was also reduced towards the late stage of amyotrophic lateral sclerosis in the spinal cord tissue of an amyotrophic lateral sclerosis-induced mouse model (see Example 5).

The above-described results suggest that the NCKAP1 protein or a gene encoding the protein can be used as a molecular marker for predicting the prognosis of a neurodegenerative disease.

According to another embodiment of the present invention, there is provided a pharmaceutical composition for the prevention or treatment of a neurodegenerative disease, which includes the NCK-associated protein 1 (NCKAP1) protein or a gene encoding the protein as an active ingredient.

The term "prevention" as used herein means all actions that inhibit or delay the onset of a neurodegenerative disease via administration of the pharmaceutical composition according to the present invention.

The term "treatment" as used herein means all actions that improve or beneficially change the symptoms of a neurodegenerative disease via administration of the pharmaceutical composition according to the present invention.

In the present invention, a function restoration effect through regulation of the expression level of the NCKAP1 gene was confirmed in microglia derived from amyotrophic lateral sclerosis or Alzheimer's disease patients having phagocytic dysfunction.

In one embodiment of the present invention, microglia derived from amyotrophic lateral sclerosis or Alzheimer's disease patients showing normal phagocytic function or phagocytic dysfunction were observed, and it was confirmed that, when the expression of the NCKAP1 gene of each case was knocked down or overexpressed in the cells, the normal phagocytic function was deteriorated by NCKAP1 knockdown and the phagocytic function was restored by the overexpression of the gene (see Examples 6 and 7).

In another embodiment of the present invention, as a result of analyzing by which mechanism the regulation of phagocytosis by NCKAP1 is caused, a change in F-actin expression of microglia according to an expression level of the gene was confirmed, and thus it was confirmed that phagocytosis was regulated by regulating actin polymerization, and it was also confirmed that the gene was involved in phagocytic cup formation (see Example 8).

These results confirm that NCKAP1 activates the phagocytic function in microglia derived from neurodegenerative disease patients, and thus the NCKAP1 protein or a gene encoding the protein may be usefully applied to prevent or treat neurodegenerative diseases.

The pharmaceutical composition according to the present invention includes, as an active ingredient, the NCKAP1 protein or a gene encoding the protein, and may further include a pharmaceutically acceptable carrier. Such pharmaceutically acceptable carriers are commonly used in preparations, and include, but are not limited to, a saline solution, sterile water, Ringer's solution, buffered saline, cyclodextrin, a dextrose solution, a maltodextrin solution, glycerol, ethanol, and liposomes, and as needed, may further include other general additives, such as an antioxidant, buffer, and the like. In addition, the pharmaceutical composition may be formulated as injectable preparations such as an aqueous solution, a suspension, and an emulsion, pills, capsules, granules, or tablets by additionally adding a diluent, a dispersant, a surfactant, a binder, a lubricant, and the like. Suitable pharmaceutically acceptable carriers may be formulated according to respective ingredients using methods disclosed in Remington's document. The pharmaceutical composition of the present invention is not particularly limited in terms of formulations, but may be formulated as an injection, an inhalant, a preparation for external application to the skin, or the like.

The pharmaceutical composition of the present invention may be administered orally or parenterally (for example, intravenously, subcutaneously, intraperitoneally or topically) according to the desired method, but preferably may be orally administered, and a dose thereof may vary depending on the condition and body weight of a patient, the severity of disease, drug form, administration route, and administration time, but may be appropriately selected by those of ordinary skill in the art.

The pharmaceutical composition according to the present invention is administered in a pharmaceutically effective amount. The term "pharmaceutically effective amount" as used herein refers to an amount sufficient to treat or diagnose diseases at a reasonable benefit/risk ratio applicable to medical treatment or diagnosis, and an effective dosage level may be determined according to factors including type of diseases of patients, the severity of disease, the activity of drugs, sensitivity to drugs, administration time, administration routes, excretion rate, treatment period, and simultaneously used drugs, and other factors well known in the medical field. The pharmaceutical composition according to the present invention may be administered as an individual therapeutic agent or in combination with other therapeutic agents, and may be administered sequentially or simultaneously in combination therewith, and may be administered in a single dose or multiple doses. It is important to administer the pharmaceutical composition in the minimum amount that enables achievement of the maximum effects without side effects in consideration of all the above-described factors, and this may be easily determined by those of ordinary skill in the art.

In particular, an effective amount of the pharmaceutical composition according to the present invention may vary according to age, gender, condition, and body weight of a patient, the absorption, inactivity, and excretion rate of active ingredients in the body, the type of disease, and simultaneously used drugs, and the pharmaceutical composition may be administered in an amount of 0.001 mg to 150 mg, preferably 0.01 mg to 100 mg, per body weight (1 kg) daily or every other day, or once to three times a day. However, the dosage may be increased or decreased according to administration route, the severity of obesity, gender, body weight, age, and the like, and thus the dosage is not intended to limit the scope of the present invention in any way.

According to another embodiment of the present invention, there is provided a method of screening for a neurodegenerative disease therapeutic material, including: treating cells with a candidate in vitro; measuring the expression or activity of the NCKAP1 gene of the cells; and selecting, as a neurodegenerative disease therapeutic material, a material that increases the expression or activity of NCKAP1 compared to a group not treated with the candidate.

The cells may be microglia derived from neurodegenerative disease patients, but the present invention is not limited thereto.

The candidate may be selected from the group consisting of compounds, microbial cultures or extracts, natural extracts, nucleic acids, and peptides, but the present invention is not limited thereto.

The expression or activity of the NCKAP1 gene may be measured using one or more methods selected from the group consisting of PCR, a microarray, northern blotting, western blotting, ELISA, immunoprecipitation, immunohistochemistry, and immunofluorescence.

According to another embodiment of the present invention, there is provided a method of preventing or treating a neurodegenerative disease, including administering the pharmaceutical composition to an individual.

The term "individual" as used herein refers to a subject in need of treatment of a disease and more particularly, includes mammals such as humans, non-human primates, mice, rats, dogs, cats, horses, and cows.

According to another embodiment of the present invention, there is provided a use of the composition for preventing or treating a neurodegenerative disease.

Hereinafter, exemplary examples will be described to aid in understanding of the present invention. However, the following examples are provided to facilitate the understanding of the present invention and are not intended to limit the scope of the present invention.

EXAMPLES

Example 1. Experimental Preparation and Experimental Method 1-1. Recruitment of Subject This study was conducted after approval of Ethics Committee of the Hanyang University. Specifically, the inventors of the present invention enrolled 11 amyotrophic lateral sclerosis (ALS) patients (6 with slow progression and 5 with rapid progression) diagnosed with sporadic ALS according to the revised E1 Escorial criteria, which are ALS diagnosis criteria, and two age-matched healthy adult volunteers, and it was confirmed that both the volunteers and the ALS patients had no ongoing infectious disease. The 11 ALS patients were clinically confirmed as an early stage (ALS Functional Rating Scale-Revised (ALSFRS-R) score: 29-41), and disease progression was determined as the changes in the AALS score, changes in time, comparing the initial evaluation with the evaluation at the time of collection or with the evaluation at the end of analysis. Rapidly progressing patients were defined as those progressing at a rate of greater than or equal to 1.5 delta ALSERS-R score/month and slowly progressing patients were those progressing at a rate of less than 0.5 delta ALSFRS-R score/month at the time of blood collection. In addition, blood samples were collected to establish induced microglia-like (iMG) cells from the patients after obtaining written informed consent. Information of the patients who participated in this study is shown in Table 1 and FIG. 1.

TABLE 1

| Patients | Age (2016) | Sex | Age of onset (yr) | ALSFRS-R score | ALSFRS/mon | Site of onset |
|---|---|---|---|---|---|---|
| S1 | 68 | F | 63 | 41 | 0.18 | Lt. U/Ext. distal |
| S2 | 63 | M | 55 | 37 | 0.14 | Rt. L/Ext. |
| S3 | 60 | M | 56 | 44 | 0.2 | Axial wk. |
| S4 | 49 | F | 46 | 39 | 0.36 | Lt. U/Ext. distal |
| S5 | 50 | M | 47 | 46 | 0.33 | Rt. u/Ext. prox |
| S6 | 61 | F | 56 | 45 | 0.11 | Rt. u/Ext. distal |
| R1 | 57 | M | 56 | 42 | 1.5 | both u/Ext. (prox) |
| R2 | 49 | F | 47 | 39 | 1.8 | Rt. L/Ext. |
| R3 | 57 | M | 55 | 29 | 1.73 | Dysarthria, Rt. u/Ext. (distal) |
| R4 | 76 | M | — | — | — | |
| R5 | 49 | M | 47 | 37 | 1.57 | Dysarthria, Lt. U/Ext. |

1-2. Generation of Induced Microglia-Like (IMG) Cells from PBMCs

To generate iMG cells from peripheral blood mononuclear cells (PBMCs), 10 cc of peripheral blood was collected using heparinized tubes from the healthy adult volunteers and the 11 ALS patients of Example 1-1. Next, peripheral blood mononuclear cells were isolated from the peripheral blood through Histopaque-1077 (Sigma Chemical Co., St. Louis, MO) density gradient centrifugation, and then cultured in RPMI-1640 (Nacalai Tesque, Kyoto, Japan) medium containing 10% heat-inactivated fetal bovine serum (FBS, Endotoxin 5 0.692 EU/ml, Japan Bio Serum, Hiroshima, Japan), and 1% antibiotic/antimycotic (Invitrogen, Carlsbad, CA). The cultured PBMCs were then plated onto the culture chamber at a density of 500,000 cells/ml and incubated overnight in standard culture conditions (37° C., 5% $CO_2$), and then the medium was carefully aspirated and monocytes, which are adherent cells, were cultured using RPMI-1640 Glutamax (Life Technologies, Carlsbad, CA, USA) medium supplemented with 1% antibiotic/antimycotic, recombinant human GM-CSF (10 ng/ml; R&D Systems, Minneapolis, MN), and recombinant human IL-34 (100 ng/ml; R&D Systems), thereby obtaining induced microglia-like cells (iMG cells). After 14 days of culture, the culture plate was washed thoroughly to remove unbound cells, a fresh medium was added, and the cells were harvested or used for functional analysis up to 21 days.

1-3. Immunocytochemistry

P2ry12 and Iba-1 were used as microglia phenotypic markers to verify whether the iMG cells produced using the method of Example 1-2 had the characteristics of microglia. More specifically, the iMG cells were washed with PBS and fixed in 4% formaldehyde, permeabilized with 0.1% Triton X-100 for 5 min. And indirect immunostaining was performed using a rabbit anti-P2ry12 antibody (#ab86195, 1:100, Abcam) and a mouse anti-Iba-1 antibody (#ab15690, 1:100, Abcam). Specifically, cells were incubated in primary antibodies diluted in 0.1% Triton-X 100 in PBS containing 5% normal goat serum at 4° C. overnight. Next, the cells were rinsed three times for 5 minutes using PBS (−), and then reacted with a secondary antibody (Invitrogen, CA, USA) conjugated with anti-rabbit Alexa 546 and anti-mouse Alexa 488. The protein was then visualized using a donkey anti-rabbit immunoglobulin G antibody (1:400 dilution; Invitrogen) conjugated with rhodamine-phalloidin according to the manufacturer's protocol. Meanwhile, the cells were counterstained with 4′,6-diamidino-2-phenylindole (DAPI; Sigma, MO, USA), and then mounted with Fluoromount-G (Cytomation; Dako). Fluorescence images were taken using a confocal microscope (TCS SP5, Leica, Wetzlar, Germany).

1-4. Quantitative Real Time-Polymerase Chain Reaction (qRT-PCR)

Cells were treated with a TRIzol (Invitrogen, Carlsbad, CA, USA) reagent to extract total RNA, and the concentration and purity of RNA were measured using Nanodrop (Thermo Scientific, ND-2000). The extracted RNA was used to synthesize cDNA using an EcoDry™ cDNA kit (Clontech, CA, USA), followed by real-time polymerase chain reaction to measure mRNA expression levels of CD11b (Qiagen, Germany, PPH00644F), CD45 (Qiagen, Germany, PPH01510C), P2ry12 (Qiagen, Germany, PPH02545B), Olfm13 (Qiagen, Germany, PPH07681A), TGF-(Qiagen, Germany, PPH00237C), CD206 (Qiagen, Germany, PPH09939B), Tmem119 (Qiagen, Germany, PPH21875A), Nckap1 (Qiagen, Germany, PPH15666A), mNckap1 (Qiagen, Germany, PPM26732A), and GAPDH (Qiagen, Germany, PPH00150F). More specifically, cDNA was amplified using Power SYBR Green PCR Master Mix with primers specific to each gene in an Applied Biosystems Step One Plus™ system (Life Technologies, USA) at 95° C. for 10 min, followed by 40 cycles of 15 s at 95° C. and 1 min at 60° C. Melting curves were generated during the amplification reaction to verify the specificity of the amplification, and the relative quantity (RQ) was calculated by a $2^{-\Delta\Delta Ct}$ method using GAPDH as an interval standard control. The experiment was independently repeated three times using the above method to obtain results.

1-5. Phagocytosis Assay

To quantify the phagocytosis of microglia, iMG cells cultured for 21 days according to the method of Example 1-2 were treated with 4 μl of red fluorescence latex beads (2 μm, Sigma-Aldrich, St. Louis, Missouri, USA) and incubated for 4 hours in a 37° C. incubator. Next, treatment with 2 ml of cold PBS was performed to stop phagocytic activity, and then the cells were washed twice with ice cold PBS, fixed, and counterstained with DAPI. The cells were then observed and analyzed using a confocal microscope (TCS SP5, Leica, Wetzlar, Germany), and the number of phagocytosed beads per cell was considered to indicate phagocytic activity.

1-6. Library Preparation and RNA Sequencing

For RNA extracted from a control and experimental groups, libraries were prepared using the Sense 3′ mRNA-Seq library Preparation Kit (Lexogen, Inc. Austria) according to the manufacturer's instructions. Briefly, 500 ng of total RNA was prepared for each group, and the reverse transcription reaction was performed by hybridizing oligo-dT primers containing Illumina-compatible sequences at the 5′-end of the RNA. After degradation of the RNA template, second strand synthesis was allowed to be carried out using a random primer comprising an Illumina-compatible linker sequence at the 5′-end thereof. Double-stranded libraries were purified using magnetic beads to remove all reaction components. In addition, the libraries were amplified to add the entire adapter sequence required for cluster generation. The completed libraries were purified by PCR and subjected to high-throughput sequencing with single-terminal 75 sequencing using NextSeq 500 (Illumina, Inc., USA).

1-7. Analysis of Sequencing Results

Sense 3′ mRNA-sequence reads were aligned using Bowtie2 version 2.1.0 (Langmead and Salzberg, 2012). Bowtie2 indices were prepared from genome assembly sequences or representative transcript sequences for genomic and transcript alignments. Alignment files were used to collect transcripts, estimate the expression levels thereof, and detect differential expression levels of genes. Differentially expressed genes were determined based on the coefficients of unique and multiple alignments using EdgeR within R version 3.2.2 (R Development Core Team (2011), R: language and environment for statistical computing, Vienna, Austria: R Foundation for statistical computing. ISBN: 3-900051-07-0, available online at R-project.org) using BIOCONDUCTOR version 3.0.

The read count (RT) data were processed based on a global normalization method using Genowiz™ version 4.0.5.6 (Ocimum Biosolutions, India). Gene classification was based on search results using DAVID (david.abcc.ncifcrf.gov) and the Medline database (ncbi.nlm.nih.gov). In addition, sample and gene clustering were performed using MeV 4.9.0, and hierarchical cluster analysis was performed by measuring the distance with average correlation using a Euclidean distance correlation, and clusters and heat maps were visualized through MeV 4.9.0.

1-8. Production of Transgenic SOD1-G93A Mice

B6SJL-Tg (SOD1-G93A) 1Gur/J mice were purchased from Jackson Laboratory (Bar Harbor, ME, USA) and were bred according to the supplier's protocol under a 12-hour light-dark cycle before the experiment. The presence of human G93A transgene was confirmed by polymerase chain reaction (PCR) and the transgene copy number was evaluated. In mice with this strain, early and late symptoms of amyotrophic lateral sclerosis are known to occur at about day 77 and about day 136, and thus the inventors of the present invention divided the SOD1-G93A mice into three groups, followed by evaluation at each time point, i.e., day 60 (no symptoms), day 90 (early symptoms), and day 120 (late symptoms). As wild type (WT) mice, B6SJLF1/J was purchased and used as a control. All animal experiments were conducted with the approval of the Institutional Animal Care and Use Committee of Hanyang University.

1-9. Intracellular Manipulation of Overexpression and Expression Inhibition of NCKAP1 Gene To overexpress or knock down the human NCKAP1 gene in cells, pLenti-C-mGFP-Human NCK-associated protein 1 (NCKAP1, NM_013436) cDNA ORF clone (OriGene Technologies, Rockville, MD, USA) or pGFP-C-shLenti-NCKAP1 Human shRNA lentiviral particles (Gene ID 10787, OriGene Technologies) were introduced into the cells 2 days before analysis. Gene knockdown efficiency was verified through qRT-PCR and by measuring protein expression levels.

1-10. Real-Time Imaging of Cell Phagocytosis

The cultured iMG cells were grown in an imaging dish (chamber slide Lab-Tek II 4, Fisher), and then for imaging of the cytoskeleton of living cells, the iMG cells were labeled using a 100 nM SiR-actin dye (Cytoskeleton Inc., North America, USA, and CA) based on a silicon rhodamine fluorophore and phalloidin, which is a F-actin-binding small molecule. The cells were then washed twice with PBS, the medium was replaced with a fresh medium, and then to visualize phagocytosis, the cells were treated with 3 μl of latex beads (1.1 μm, Sigma-Aldrich, St. Louis, Missouri, USA) before analysis. Real-time images were taken one frame every one minute and 30 seconds for 4 hours, and photographing was performed using a DeltaVision fluorescence microscope system (Applied Precision) installed at the Hanyang Center for Research Facilities, Seoul.

1-11. Statistical Analysis

The experimental results were expressed as mean±SEM. Significance between groups was evaluated by a Student's t test and one way-ANOVA using Prism Version 7.0 software, and P-value<0.05 was considered significant.

Example 2. Phenotypic Analysis of Microglial Derived from Peripheral Blood Derived from Amyotrophic Lateral Sclerosis Patients It was examined whether the iMG cells derived from peripheral blood derived from amyotrophic lateral sclerosis patients having different degrees of disease progression (slow/rapid progression) according to the methods of Examples 1-1 and 1-2 had microglial phenotypes. To this end, the iMG cells were subjected to immunocytochemistry and real-time polymerase chain reaction (qRT-PCR) according to the methods of Examples 1-3 and 1-4 to measure the expression levels of P2ry12, iba-1, Olfml3, Tgf-βr1, Tmem119, CD11b, and CD45, which are core genes of microglia.

First, as a result of performing immunocytochemistry to observe the expression of the P2ry12 and iba-1 proteins, as illustrated in FIG. 2A, it was confirmed that, similar to normal control-derived iMG cells (HC), the proteins were expressed in both cases (ALS(S) and ALS(R)) of iMG cells derived from peripheral blood derived from amyotrophic lateral sclerosis patients having slow and rapid progression rates. In addition, as a result of measuring the mRNA expression level of each gene through qRT-PCR, as illustrated in FIGS. 2B and 2C, it was confirmed that, when performing a relative comparison based on the expression value of monocytes, the mRNA levels of P2ry12, iba-1, Olfm13, Tgf-βr1, Tmem119, and CD11b were increased, and the mRNA level of CD45 was reduced.

These results indicate that the iMG cells derived from peripheral blood derived from amyotrophic lateral sclerosis patients have the characteristics of microglia.

Example 3. Phagocytosis Assay of Microglial Derived from Peripheral Blood Derived from Amyotrophic Lateral Sclerosis Patients In addition to the results of Example 2, the phagocytic function of microglia derived from amyotrophic lateral sclerosis patients was analyzed. To determine whether there is a difference according to the progression degree of amyotrophic lateral sclerosis, the phagocytosis of microglia (ALS (Slow) and ALS(Rapid)) derived from peripheral blood derived from amyotrophic lateral sclerosis patients having slow and rapid progression rates, respectively, was analyzed using the method of Example 1-5.

As a result, as shown in FIG. 3A, severe phagocytic dysfunction was observed in ALS(Rapid), as an immunostaining result. In addition, through FIG. 3B, red fluorescence was clearly observed only in the case of ALS(Slow), from which it was confirmed that phagocytosis actively occurred only in ALS(Slow). The above results confirmed the phagocytic function in the microglia derived from peripheral blood derived from amyotrophic lateral sclerosis patients, and such an action was observed only in amyotrophic lateral sclerosis patients having a slow progression rate.

Example 4. Analysis of Gene Expression Difference in Microglial Derived from Amyotrophic Lateral Sclerosis Patients Through RNA Sequencing Since it was confirmed through the results of Example 3 that the microglia derived from amyotrophic lateral sclerosis patients with different progression degrees exhibited different phagocytic activities, RNA sequencing was performed according to the methods of Examples 1-6 and 1-7 to perform transcript analysis of the microglia derived from patients with different degrees of disease progression.

First, as a result of showing, as a Vann diagram, the results of transcript analysis of the microglia (R/C and S/C) derived from amyotrophic lateral sclerosis patients with a rapid progression rate and a slow progression rate, respectively, as illustrated in FIG. 4A, a great number of differentially expressed genes were present. Furthermore, as a result of comparing the expression levels of transcripts related to phagocytosis, as illustrated in FIG. 4B, it was confirmed that the expression of the NCKAP1 gene was significantly reduced in the microglia (R/C) derived from amyotrophic lateral sclerosis patients having a rapid progression rate. Therefore, the inventors of the present invention conducted the following experiments to more particularly analyze the effect of the gene in amyotrophic lateral sclerosis.

Example 5. Analysis of NCKAP1 Expression Levels in Amyotrophic Lateral Sclerosis Patients and Animal Model 5-1. Analysis of NCKAP1 Expression Levels in Microglia Derived from Amyotrophic Lateral Sclerosis Patients To determine the expression level of the NCKAP1 gene found in Example 4 in microglia derived from amyotrophic lateral sclerosis patients with different degrees of disease progression, qRT-PCR and immunocytochemistry were performed to measure the mRNA and protein expression levels of the gene.

As a result, it was observed as shown in FIG. 5A that the mRNA expression level of NCKAP1 was greatly reduced in microglia (ALS(Rapid)) derived from patients having a rapid progression rate, and it was confirmed as shown in FIG. 5B that, even at the protein level, the protein expression level was very low in microglia (ALS i-MG (R)) derived from patients having a rapid progression rate.

5-2. Analysis of mRNA Expression Level of NCKAP1 in Spinal Cord Tissue of Amyotrophic Lateral Sclerosis Mouse Model Furthermore, the inventors of the present invention measured the expression level of NCKAP1 mRNA in the spinal cord tissue of the amyotrophic lateral sclerosis mouse model produced using the method of Example 1-8.

As a result, it was confirmed as shown in FIG. 6 that the expression level of the gene was greatly reduced at the late stage of amyotrophic lateral sclerosis of the mice.

Example 6. Analysis of Change in Phagocytic Function of Microglia Derived from Amyotrophic Lateral Sclerosis Patients According to Regulation of NCKAP1 Expression The inventors of the present invention tried to determine whether the phagocytosis of microglia derived from amyotrophic lateral sclerosis patients is changed according to the expression level of NCKAP1, based on the results of Examples 4 and 5. To this end, after overexpressing or knocking down NCKAP1 in the microglia according to the method of Example 1-9, a change in the phagocytic function of the cells was analyzed by real-time imaging.

As a result, as illustrated in FIG. 7, when the expression of NCKAP1 was inhibited using shRNA (shNCKAP1) in microglia (ALS (S)-iMG) derived from patients having a slow progression rate, it was observed that the phagocytosis of the cells was significantly reduced, contrary to the results of Example 3. In contrast, it was confirmed that, when NCKAP1 was overexpressed (O/E) in microglia (ALS (R)-iMG) derived from patients having a rapid progression rate, the phagocytic function was restored.

Through the above results, it was confirmed that the NCKAP1 gene could regulate the phagocytic function of microglia derived from amyotrophic lateral sclerosis patients.

Example 7. Analysis of Phagocytosis of Microglia Derived from Peripheral Blood Derived from Alzheimer's Disease Patients and Regulatory Function by NCKAP1

7-1. Observation of Phagocytosis of Microglia Derived from Peripheral Blood Derived from Alzheimer's Disease Patients The inventors of the present invention examined whether the NCKAP1 gene affects the phagocytic function in Alzheimer's disease, which is another neurodegenerative disease. Specifically, similarly to Example 3, to investigate whether the phagocytic function is different according to the progression of the disease, the phagocytosis of microglia (AD(S)-iMG and AD(R)-iMG) derived from peripheral blood derived from Alzheimer's disease patients having slow and rapid progression rates, respectively, was observed real time according to the method of Example 1-9.

As a result, as shown in FIG. 8, similar to the amyotrophic lateral sclerosis patients, severe phagocytic dysfunction was observed in microglia (AD(R)-iMG) derived from Alzheimer's disease patients having a rapid progression rate.

7-2. Analysis of Change in Phagocytic Function of Microglia Derived from Alzheimer's Disease Patients According to Regulation of NCKAP1 Expression It was determined whether the phagocytosis of microglia derived from Alzheimer's disease patients is changed according to the expression level of NCKAP1, based on the results of Example 7-1. To this end, after overexpressing or knocking down NCKAP1 in the microglia according to the method of Example 1-9, changes in the phagocytic function of the cells were analyzed by real-time imaging.

As a result, as illustrated in FIG. 9, when the expression of NCKAP1 was inhibited using shRNA (shNCKAP1) in microglia (AD (S)-iMG) derived from patients having a slow progression rate, it was observed that the phagocytosis of the cells was significantly reduced, contrary to the results of Example 7-1. In contrast, it was confirmed that, when NCKAP1 was overexpressed (O/E) in microglia (AD (R)-iMG) derived from patients having a rapid progression rate, the phagocytic function was restored.

Through the above results, it was confirmed that the NCKAP1 gene could regulate the phagocytic function of microglia derived from Alzheimer's disease patients.

Example 8. Analysis of Phagocytic Regulation Mechanism by NCKAP1

8-1. Confirmation of Change in F-Actin Expression According to Regulation of NCKAP1 Expression Since the inventors of the present invention confirmed through the above example results that NCKAP1 could regulate the phagocytic function of microglia derived from patients with amyotrophic lateral sclerosis and Alzheimer's disease, to determine whether the gene regulates the phagocytosis of the cells by being involved in cellular actin polymerization, first, a change in F-actin expression according to the regulation of NCKAP1 expression in Hela, which is a human cervical cancer cell line, was analyzed.

As a result, as result of observing phalloidin images which show the expression level of F-actin when NCKAP1 was overexpressed (GFP-NCKAP1) or knocked down (shNCKAP1), it was confirmed, as shown in FIG. 10A, that F-actin expression was increased upon NCKAP1 overexpression, whereas F-actin expression was reduced when the expression of NCKAP1 was knocked down.

Based on the above results, it was also determined whether a change in F-actin expression was induced according to the expression level of NCKAP1 in microglia derived from amyotrophic lateral sclerosis patients. To this end, based on the results of Example 6, the change in F-actin expression was observed after knocking down the expression of NCKAP1 in microglia (ALS (S)+shNCKAP1) derived from patients having a slow progression rate or overexpressing NCKAP1 in microglia (ALS (R)+NCKAP1 O/E) derived from patients having a rapid progression rate.

As a result, it was confirmed as shown in FIG. 10B that, while the F-actin expression was reduced in the case of ALS (S)+shNCKAP1, the F-actin expression was increased in the case of ALS (R)+NCKAP1 O/E.

These results indicate that NCKAP1 regulates phagocytosis by being involved in actin polymerization in patient-derived microglia.

8-2. Confirmation of NCKAP1 Function for Phagocytic Cup Formation According to Actin Dynamics Since it was confirmed through the results of Example 8-1 that NCKAP1 was involved in actin polymerization, it was further analyzed whether NCKAP1 affected phagocytic cup formation by actin dynamics.

As a result, as illustrated in FIG. 11, it was confirmed through immunostaining results that F-actin expression and NCKAP1 expression were exhibited in the same manner in a phagocytic cup portion corresponding to the position of beads ingested by the phagocytosis of patient-derived microglia, through which it was confirmed that NCKAP1 was involved in phagocytic cup formation.

The above description of the present invention is provided only for illustrative purposes, and it will be understood by one of ordinary skill in the art to which the present invention pertains that the invention may be easily modified into other specific forms without departing from the technical spirit or essential characteristics thereof. Thus, the embodiments described herein should be considered in an illustrative sense only and not for the purpose of limitation.

INDUSTRIAL APPLICABILITY

The present invention is a technology for developing a therapeutic agent for neurodegenerative diseases by selectively regulating only specific signal transduction related to the phagocytosis of microglia using the NCKAP1 protein that regulates the phagocytic function in microglia, or a gene encoding the protein, and thus enables the development of a therapeutic agent with high safety and efficiency compared to existing therapeutic agents for inducing immunosuppression. In addition, the NCKAP1 gene can be usefully applied as a marker for predicting the prognosis of a neurodegenerative disease to predict the progression rate of the disease and treatment results, and thus the technology according to the present invention can be widely used in predicting the prognosis of neurodegenerative diseases and the therapeutic agent development field.

The invention claimed is:

1. A method for determining a rapid progression rate of amyotrophic lateral sclerosis (ALS) in a test subject who has been diagnosed with ALS and restoring phagocytic function of microglia in the test subject with the rapid progression rate of the ALS, the method comprising:
    measuring a level of a NCK-associated protein 1 (NCKAP1) protein or an mRNA thereof in the microglia derived from a biological sample isolated from the test subject diagnosed with ALS;
    comparing the level of the NCKAP1 protein or the mRNA thereof in the microglia derived from the biological sample of the test subject with a level of the NCKAP1 protein or mRNA thereof in the microglia derived from the biological sample isolated from a healthy subject without ALS;
    determining whether the test subject has a rapid or slow progression rate based on the level of the NCKAP1 protein or the mRNA thereof compared to that of the healthy subject without ALS,
    wherein a lower level of the NCKAP1 protein or the mRNA thereof in the biological sample derived from the microglia of the test subject compared to that of the healthy subject is an indicator of the rapid progression rate,
    wherein a higher or equivalent level of the NCKAP 1 protein or the mRNA thereof in the microglia derived from the biological sample of the test subject compared to that of the healthy subject is an indicator of the slow progression rate; and
    wherein the progression rate is expressed as a change in amyotrophic lateral sclerosis functional rating scale-revised (ALSFRS-R) score (delta ALSFRS-R), the rapid progression rate has the delta ALSFRS-R score/month of greater than or equal to 1.5 and the slow progression rate has the delta ALSFRS-R score/month of less than 0.5, and
    administering the NCKAP1 NCKAP1 protein or the NCKAP1 protein-encoding gene to the test subject determined to have the rapid progression rate of the ALS and thereby restoring phagocytic function of the microglia in the test subject with the rapid progression rate of the ALS.

2. The method of claim 1, wherein the NCKAP 1 protein consists of the amino acid sequence of SEQ ID NO: 1.

3. The method of claim 1, wherein the gene encoding the protein consists of the nucleotide sequence of SEQ ID NO: 2.

* * * * *

UNITED STATES PATENT AND TRADEMARK OFFICE
CERTIFICATE OF CORRECTION

| | | |
|---|---|---|
| PATENT NO. | : 11,958,885 B2 | Page 1 of 1 |
| APPLICATION NO. | : 16/651783 | |
| DATED | : April 16, 2024 | |
| INVENTOR(S) | : Seung Hyun Kim et al. | |

It is certified that error appears in the above-identified patent and that said Letters Patent is hereby corrected as shown below:

On the Title Page

Item [73] insert --CHA UNIVERSITY INDUSTRY-ACADEMIC COOPERATION FOUNDATION, Pocheon-si, Gyeonggi-Do (KR)--

Signed and Sealed this
Twenty-ninth Day of July, 2025

Coke Morgan Stewart
*Acting Director of the United States Patent and Trademark Office*

SEQUENCE LISTING

<160> NUMBER OF SEQ ID NOS: 2

<210> SEQ ID NO 1
<211> LENGTH: 1128
<212> TYPE: PRT
<213> ORGANISM: Homo sapiens
<220> FEATURE:
<223> OTHER INFORMATION: NCKAP1

<400> SEQUENCE: 1

```
Met Ser Arg Ser Val Leu Gln Pro Ser Gln Gln Lys Leu Ala Glu Lys
1               5                   10                  15

Leu Thr Ile Leu Asn Asp Arg Gly Val Gly Met Leu Thr Arg Leu Tyr
            20                  25                  30

Asn Ile Lys Lys Ala Cys Gly Asp Pro Lys Ala Lys Pro Ser Tyr Leu
        35                  40                  45

Ile Asp Lys Asn Leu Glu Ser Ala Val Lys Phe Ile Val Arg Lys Phe
    50                  55                  60

Pro Ala Val Glu Thr Arg Asn Asn Asn Gln Gln Leu Ala Gln Leu Gln
65                  70                  75                  80

Lys Glu Lys Ser Glu Ile Leu Lys Asn Leu Ala Leu Tyr Tyr Phe Thr
                85                  90                  95

Phe Val Asp Val Met Glu Phe Lys Asp His Val Cys Glu Leu Leu Asn
            100                 105                 110

Thr Ile Asp Val Cys Gln Val Phe Phe Asp Ile Thr Val Asn Phe Asp
        115                 120                 125

Leu Thr Lys Asn Tyr Leu Asp Leu Ile Ile Thr Tyr Thr Thr Leu Met
    130                 135                 140
```

-continued

```
Ile Leu Leu Ser Arg Ile Glu Glu Arg Lys Ala Ile Ile Gly Leu Tyr
145                 150                 155                 160

Asn Tyr Ala His Glu Met Thr His Gly Ala Ser Asp Arg Glu Tyr Pro
            165                 170                 175

Arg Leu Gly Gln Met Ile Val Asp Tyr Glu Asn Pro Leu Lys Lys Met
        180                 185                 190

Met Glu Glu Phe Val Pro His Ser Lys Ser Leu Ser Asp Ala Leu Ile
        195                 200                 205

Ser Leu Gln Met Val Tyr Pro Arg Arg Asn Leu Ser Ala Asp Gln Trp
210                 215                 220

Arg Asn Ala Gln Leu Leu Ser Leu Ile Ser Ala Pro Ser Thr Met Leu
225                 230                 235                 240

Asn Pro Ala Gln Ser Asp Thr Met Pro Cys Glu Tyr Leu Ser Leu Asp
            245                 250                 255

Ala Met Glu Lys Trp Ile Ile Phe Gly Phe Ile Leu Cys His Gly Ile
        260                 265                 270

Leu Asn Thr Asp Ala Thr Ala Leu Asn Leu Trp Lys Leu Ala Leu Gln
        275                 280                 285

Ser Ser Ser Cys Leu Ser Leu Phe Arg Asp Glu Val Phe His Ile His
290                 295                 300

Lys Ala Ala Glu Asp Leu Phe Val Asn Ile Arg Gly Tyr Asn Lys Arg
305                 310                 315                 320

Ile Asn Asp Ile Arg Glu Cys Lys Glu Ala Ala Val Ser His Ala Gly
            325                 330                 335

Ser Met His Arg Glu Arg Arg Lys Phe Leu Arg Ser Ala Leu Lys Glu
        340                 345                 350

Leu Ala Thr Val Leu Ser Asp Gln Pro Gly Leu Leu Gly Pro Lys Ala
        355                 360                 365

Leu Phe Val Phe Met Ala Leu Ser Phe Ala Arg Asp Glu Ile Ile Trp
        370                 375                 380

Leu Leu Arg His Ala Asp Asn Met Pro Lys Lys Ser Ala Asp Asp Phe
385                 390                 395                 400

Ile Asp Lys His Ile Ala Glu Leu Ile Phe Tyr Met Glu Glu Leu Arg
            405                 410                 415

Ala His Val Arg Lys Tyr Gly Pro Val Met Gln Arg Tyr Tyr Val Gln
        420                 425                 430

Tyr Leu Ser Gly Phe Asp Ala Val Leu Asn Glu Leu Val Gln Asn
        435                 440                 445

Leu Ser Val Cys Pro Glu Asp Glu Ser Ile Ile Met Ser Ser Phe Val
450                 455                 460

Asn Thr Met Thr Ser Leu Ser Val Lys Gln Val Glu Asp Gly Glu Val
465                 470                 475                 480

Phe Asp Phe Arg Gly Met Arg Leu Asp Trp Phe Arg Leu Gln Ala Tyr
            485                 490                 495

Thr Ser Val Ser Lys Ala Ser Leu Gly Leu Ala Asp His Arg Glu Leu
        500                 505                 510

Gly Lys Met Met Asn Thr Ile Ile Phe His Thr Lys Met Val Asp Ser
        515                 520                 525

Leu Val Glu Met Leu Val Glu Thr Ser Asp Leu Ser Ile Phe Cys Phe
        530                 535                 540

Tyr Ser Arg Ala Phe Glu Lys Met Phe Gln Gln Cys Leu Glu Leu Pro
545                 550                 555                 560
```

```
Ser Gln Ser Arg Tyr Ser Ile Ala Phe Pro Leu Leu Cys Thr His Phe
            565                 570                 575
Met Ser Cys Thr His Glu Leu Cys Pro Glu Glu Arg His His Ile Gly
            580                 585                 590
Asp Arg Ser Leu Ser Leu Cys Asn Met Phe Leu Asp Glu Met Ala Lys
            595                 600                 605
Gln Ala Arg Asn Leu Ile Thr Asp Ile Cys Thr Glu Gln Cys Thr Leu
        610                 615                 620
Ser Asp Gln Leu Leu Pro Lys His Cys Ala Lys Thr Ile Ser Gln Ala
625                 630                 635                 640
Val Asn Lys Lys Ser Lys Lys Gln Thr Gly Lys Lys Gly Glu Pro Glu
                645                 650                 655
Arg Glu Lys Pro Gly Val Glu Ser Met Arg Lys Asn Arg Leu Val Val
            660                 665                 670
Thr Asn Leu Asp Lys Leu His Thr Ala Leu Ser Glu Leu Cys Phe Ser
        675                 680                 685
Ile Asn Tyr Val Pro Asn Met Val Val Trp Glu His Thr Phe Thr Pro
    690                 695                 700
Arg Glu Tyr Leu Thr Ser His Leu Glu Ile Arg Phe Thr Lys Ser Ile
705                 710                 715                 720
Val Gly Met Thr Met Tyr Asn Gln Ala Thr Gln Glu Ile Ala Lys Pro
                725                 730                 735
Ser Glu Leu Leu Thr Ser Val Arg Ala Tyr Met Thr Val Leu Gln Ser
            740                 745                 750
Ile Glu Asn Tyr Val Gln Ile Asp Ile Thr Arg Val Phe Asn Asn Val
        755                 760                 765
Leu Leu Gln Gln Thr Gln His Leu Asp Ser His Gly Glu Pro Thr Ile
    770                 775                 780
Thr Ser Leu Tyr Thr Asn Trp Tyr Leu Glu Thr Leu Leu Arg Gln Val
785                 790                 795                 800
Ser Asn Gly His Ile Ala Tyr Phe Pro Ala Met Lys Ala Phe Val Asn
                805                 810                 815
Leu Pro Thr Glu Asn Glu Leu Thr Phe Asn Ala Glu Gly Tyr Ser Asp
            820                 825                 830
Ile Ser Glu Met Arg Ser Leu Ser Glu Leu Leu Gly Pro Tyr Gly Met
        835                 840                 845
Lys Phe Leu Ser Glu Ser Leu Met Trp His Ile Ser Ser Gln Val Ala
    850                 855                 860
Glu Leu Lys Lys Leu Val Val Glu Asn Val Asp Val Leu Thr Gln Met
865                 870                 875                 880
Arg Thr Ser Phe Asp Lys Pro Asp Gln Met Ala Ala Leu Phe Lys Arg
                885                 890                 895
Leu Ser Ser Val Asp Ser Val Leu Lys Arg Met Thr Ile Ile Gly Val
            900                 905                 910
Ile Leu Ser Phe Arg Ser Leu Ala Gln Glu Ala Leu Arg Asp Val Leu
        915                 920                 925
Ser Tyr His Ile Pro Phe Leu Val Ser Ile Glu Asp Phe Lys Asp
    930                 935                 940
His Ile Pro Arg Glu Thr Asp Met Lys Val Ala Met Asn Val Tyr Glu
945                 950                 955                 960
Leu Ser Ser Ala Ala Gly Leu Pro Cys Glu Ile Asp Pro Ala Leu Val
                965                 970                 975
Val Ala Leu Ser Ser Gln Lys Ser Glu Asn Ile Ser Pro Glu Glu Glu
```

```
                980               985                990
Tyr Lys Ile Ala Cys Leu Leu Met Val Phe Val Ala Val Ser Leu Pro
            995                1000                1005

Thr Leu Ala Ser Asn Val Met Ser Gln Tyr Ser Pro Ala Ile Glu Gly
        1010                1015                1020

His Cys Asn Asn Ile His Cys Leu Ala Lys Ala Ile Asn Gln Ile Ala
1025                1030                1035                1040

Ala Ala Leu Phe Thr Ile His Lys Gly Ser Ile Glu Asp Arg Leu Lys
            1045                1050                1055

Glu Phe Leu Ala Leu Ala Ser Ser Leu Leu Lys Ile Gly Gln Glu
        1060                1065                1070

Thr Asp Lys Thr Thr Arg Asn Arg Glu Ser Val Tyr Leu Leu Leu
    1075                1080                1085

Asp Met Ile Val Gln Glu Ser Pro Phe Leu Thr Met Asp Leu Leu Glu
        1090                1095                1100

Ser Cys Phe Pro Tyr Val Leu Leu Arg Asn Ala Tyr His Ala Val Tyr
1105                1110                1115                1120

Lys Gln Ser Val Thr Ser Ser Ala
            1125

<210> SEQ ID NO 2
<211> LENGTH: 4997
<212> TYPE: DNA
<213> ORGANISM: Homo sapiens
<220> FEATURE:
<223> OTHER INFORMATION: NCKAP1 mRNA

<400> SEQUENCE: 2
gcggcgagcg cctgtcaagc agtgggagga aaaagcgctt ggagccacca gcccactctt    60
aagcgaaact cgcctggaaa acaccccgcc tcccagcaga gtttctgccg gtttctttag   120
aagggtggtg cggaaaagca acttttggga acttgaagga gtggggtgtg gggcgaagtg   180
gaaagagcac acaacgcgac cccactcagt ccccgcttgg gactcccatc ccggcatcag   240
gcgtagtggg cggtccgggc cagggccagg ccagagcgg cggcggcgag gccatgccga   300
gggcccgtcg gccgcagttc cccgtccggc ctcgcggggg cgccggcgct gccgatcagg   360
tgaccgaggg cccgtccggg gctgcgggaa gcggcctcgt tctcagccgc cggagacgcc   420
gccgccgccg ccgccgccgc cacacctagt ggagcagccg ggaaggcgg ctcgttgggg   480 gctgggcgg agagcgccgg gggtgggggc ggaagggcgg cgggcggaag gcaggaggct   540
gccggggcgc gggctgctgc gggagaaggg gctccgagga gtccgccgcg gctcgctctg   600
tcgccggcgc gggattgggg cgcgagggcc atgggcgcgc tctcctaagg cggaggtcgc   660
gggcgggagg ggaggaggcc cgagagaggc tgctgcgaag gccgcgggcc cgtgactggg   720
cgcgaggcgg ccggcggcgg cggcggcacc agcaccacca tgtcgcgctc agtgctgcag   780
cccagtcagc agaagctggc ggagaagctc accatcctca cgaccgggg cgtcggcatg   840 ctcacccgcc tctacaacat caagaaggca tgtggagacc ccaaggcaaa accatcctat   900
cttatcgaca aaaaccctgga atctgctgtg aaattcatag tcagaaaatt ccctgctgta   960
gaaacccgca acaacaatca acagcttgca caactacaga agaaaaatc agagattctg   1020 aaaaatctgg cattatatta cttcacattt gtagatgtta tggaatttaa ggaccatgtt   1080
tgtgaattgc tgaatactat tgacgtttgc caagtcttct ttgatattac tgtaaacttt   1140
gatttaacaa agaactactt agatttaatt ataacctata caacactaat gatactgctg   1200
```

```
tctcgaattg aagaaaggaa ggcaatcatt ggattataca actatgccca tgaaatgact    1260
catggagcaa gtgacagaga atacccacgc cttggccaga tgattgtgga ttatgaaaac    1320
cctttaaaga agatgatgga agaatttgta ccccatagca agtctctttc agatgcacta    1380
atttctcttc aaatggtata tcctcgaagg aatctttcag ctgaccagtg gagaaatgcc    1440
cagttattga gcctcatcag tgcacctagt acaatgctta atccagcaca gtccgacact    1500
atgccttgtg aatacctctc tttggatgca atggaaaagt ggattatctt tggctttatt    1560
ttgtgccatg ggatcctaaa tactgacgct acagcactga acctttggaa actagctctt    1620
caaagtagct cttgcctctc tctctttcgg gatgaagttt tccacattca caaagctgca    1680
gaagacttat ttgtaaacat acgaggctat aataaacgta ttaatgacat aagagaatgc    1740
aaggaggcag ccgtgtcaca tgctggttca atgcacagag aaagacgcaa gttttaaga    1800 tctgcactga aggaattggc tactgtcctc tctgatcaac ctggattgct aggtcccaag    1860 gcacttttg tttttatggc attatccttt gcccgtgatg aaatcatctg gctacttcgt    1920
catgcagata acatgccaaa gaagagtgca gacgacttta tagataagca cattgctgaa    1980
ttaatatttt acatggaaga acttagagca catgtgagga aatacggacc tgtaatgcag    2040
aggtattacg tgcagtacct ttctggcttt gatgctgttg tcctcaatga actcgtgcag    2100
aatctttctg tttgccctga agatgaatca atcatcatgt cctcttttgt taacactatg    2160
acttccctaa gtgtaaaaca agttgaagat ggggaagtat ttgatttcag aggaatgaga    2220
ttagattggt ttaggttaca ggcatatact agtgtctcaa aggcttcact tggccttgca    2280
gatcacagag aacttggaaa gatgatgaat acaataattt ttcatacaaa aatggtagat    2340
tccttggtgg aaatgttggt ggaaacatca gatctctcca tattttgttt ttatagtcgt    2400
gcttttgaga agatgtttca acagtgtttg gagttaccct ctcaatcaag atactcaatt    2460
gcatttccac tactttgcac tcatttatg agttgcacgc atgaactatg tccagaagag    2520
cgacatcata ttggagatcg cagtctttcc ttatgtaata tgttcctaga tgaaatggcc    2580
aaacaagctc gaaatctcat cactgatatt tgcacagaac agtgtaccct tagtgaccag    2640
ttgctaccca agcattgtgc caaaactatc agtcaagcag tgaataagaa atcaaaaaag    2700
cagactggta agaaagggga acctgaaagg gagaaaccag gtgttgagag catgaggaaa    2760
aacaggctgg ttgtgaccaa ccttgataaa ttgcacactg cactttctga gttatgcttc    2820
tctataaatt atgtaccaaa catggtggta tgggaacata cctttacccc acgagaatat    2880
ttgacttctc atctggaaat acgctttacc aagtcaattg ttgggatgac tatgtataat    2940
caagccacac aggaaattgc aaaaccttca gaacttctaa caagtgtaag agcatacatg    3000
accgtactcc agtcaataga aaactatgtg cagattgata ttacaagagt atttaataat    3060
gtgcttcttc aacaaacaca acatttagac agtcatggag agccaaccat tacaagtcta    3120
tacacaaatt ggtatttgga aactttgtta cgacaagtca gcaatggcca tatagcatat    3180
tttcctgcaa tgaaagcgtt tgtgaactta cctacagaaa atgaattaac attcaatgca    3240
gaggaatatt ctgacatatc agaaatgagg tcattatcag aactactagg cccatatggt    3300
atgaagtttc taagtgaaag ccttatgtgg catatttcat cacaagttgc tgaacttaag    3360
aaacttgtgg tggagaatgt tgatgtgtta acacaaatga ggaccagctt tgacaaacca    3420
gaccagatgg ctgcactgtt taaaagatta tcatctgttg acagtgtctt gaagaggatg    3480
acaataattg gtgtaatttt atccttccga tcattggcac aagaagcact tagagatgtc    3540
ttatcctacc acattccttt tcttgtaagt tcaattgaag attttaagga tcacattcca    3600
```

-continued

```
agggaaactg atatgaaggt tgcaatgaat gtgtatgagt tatcatcagc tgccggatta    3660
ccttgtgaga ttgatcctgc attggtcgta gctctttctt cacaaaaatc ggaaaacatt    3720
agtccagaag aagagtataa aattgcctgc cttctcatgg tgtttgtggc agtttctttg    3780
ccaacactgg ccagtaatgt gatgtctcag tacagccctg ctatagaagg gcattgcaac    3840
aacatacatt gcttggccaa agccatcaac cagattgctg cagctttgtt tacaattcac    3900
aaaggaagca ttgaagaccg tcttaaagaa tttctggcgc ttgcatcctc cagtctactg    3960
aaaattggcc aggagacaga taaaactaca acaagaaata gagaatctgt ttatttactg    4020
ctagatatga ttgtacaaga atctccattc cttacaatgg atcttttgga atcttgtttt    4080
ccttatgtct tgctgagaaa tgcataccat gctgtctaca aacaaagtgt tacatcttct    4140
gcataaaatt acctacttaa tcaagataag cacgcatttt tgttgccttg gttttacctg    4200
tagactgtgg aactatttta ccttaagacc tgaaaaagtt ttgtggatta taaatttctt    4260
tcatacggtt gtattttctg atcattggtt tcttaatatg gttgtactac agtatacttg    4320
gttgatttag gttgcacatt cactgaattc actgagatta ttcctataat tttaaagtat    4380
catttatttg aaaaacatac attatcaaca tgtttttgat atttgataat gaaaaaaatc    4440
tttgcttgtt tatttctgaa aaagaactgt atttagtgat tattttagat agtgatatta    4500
tagtattcat ctgtgtgtaa attatttcat atagggaaga gttctgatct gtacctatgg    4560
ttcttattga aaacaacatt ggatgtgcat ttctgtgatg ttatgaatac atttctactt    4620
tattttgaaa catttgccaa actaaatact gtaacactgt ataacattta aaaatgttaa    4680
agaactgctt agtattagaa gcagatcatt tcccaaaatt ctaagagcag cagcatatgt    4740
tgttgcttgt ataaagccta gcgataattt ttagactaac ttccatggtg ccctgttggc    4800
attagcacta ccattgtacc ctgctgtata ataaacaatc ttagacattt atcaactgtt    4860
gatacaaatg ttagtcccta accactttttt atatatgttt taaattttttg aaattcaagt    4920 gtacctgcca taacataaaa taaacactag actgtatcac acttcgattg atttctttaa    4980
gatccttgga tattcgt                                                    4997
```